United States Patent
Kaiser et al.

(10) Patent No.: US 7,695,675 B2
(45) Date of Patent: Apr. 13, 2010

(54) METHOD OF INACTIVATING MICROORGANISMS IN A FLUID USING ULTRAVIOLET RADIATION

(75) Inventors: Klaus Kaiser, Cologne (DE); Hans-Juergen Henzler, Solingen (DE); Joerg Kauling, Cologne (DE); Rolf Treckmann, Cary, NC (US); Kathryn Remington, Cary, NC (US); Cynthia J. Galloway, Garner, NC (US)

(73) Assignees: Bayer Healthcare LLC, Tarrytown, NY (US); Bayer Aktiengesellschaft, Leverkusen (DE)

( * ) Notice: Subject to any disclaimer, the term of this patent is extended or adjusted under 35 U.S.C. 154(b) by 605 days.

(21) Appl. No.: 11/079,934

(22) Filed: Mar. 14, 2005

(65) Prior Publication Data

US 2007/0003430 A1    Jan. 4, 2007

Related U.S. Application Data

(63) Continuation of application No. 10/196,020, filed on Jul. 16, 2002, now abandoned, which is a continuation of application No. 09/711,780, filed on Nov. 13, 2000, now abandoned.

(51) Int. Cl.
| | |
|---|---|
| *B08B 17/00* | (2006.01) |
| *A61L 2/00* | (2006.01) |
| *B01J 19/08* | (2006.01) |
| *G01N 23/00* | (2006.01) |
| *B01D 63/00* | (2006.01) |
| *B01D 21/26* | (2006.01) |

(52) U.S. Cl. .................. 422/24; 422/1; 422/6; 422/186; 422/44; 422/905; 250/432 R; 250/455.11; 210/748; 210/319; 210/320; 210/512.3; 210/321.63; 435/302.1

(58) Field of Classification Search ..................... 422/1, 422/6, 24, 186, 44, 905; 250/432 R, 455.11; 210/748, 319, 320, 512.3, 321.63; 435/302.1
See application file for complete search history.

(56) References Cited

U.S. PATENT DOCUMENTS

| | | | | |
|---|---|---|---|---|
| 4,321,919 | A | * | 3/1982 | Edelson ...................... 604/6.08 |
| 4,769,131 | A | * | 9/1988 | Noll et al. ...................... 210/85 |
| 5,466,425 | A | * | 11/1995 | Adams ..................... 422/186.3 |
| 6,570,167 | B1 | * | 5/2003 | Bryer et al. ................. 250/431 |

FOREIGN PATENT DOCUMENTS

WO      WO 95/15294      *    6/1995

* cited by examiner

*Primary Examiner*—Jill Warden
*Assistant Examiner*—Monzer R Chorbaji
(74) *Attorney, Agent, or Firm*—Norris, McLaughlin & Marcus PA

(57) ABSTRACT

A method of inactivating microorganisms such as viruses within a fluid such as a biological fluid is disclosed. The method includes the steps of providing a UV reactor, which may take the form of an elongated generally annular reaction chamber surrounding at least one elongated UV lamp, moving the fluid within the reaction chamber in a primary flow directed along the length of the UV lamp, and inducing a circulating secondary flow within the fluid with the secondary flow being superimposed on the primary flow. As the fluid moves through the reaction chamber in the primary flow, it is circulated repeatedly toward and away from the UV lamp in the circulating secondary flow to provide uniform and controllable exposure of the entire volume of fluid to ultraviolet radiation. Microorganisms such as viruses are thus inactivated while desirable components in the fluid, such as proteins, are preserved without the use of a free radical scavenger.

11 Claims, 15 Drawing Sheets

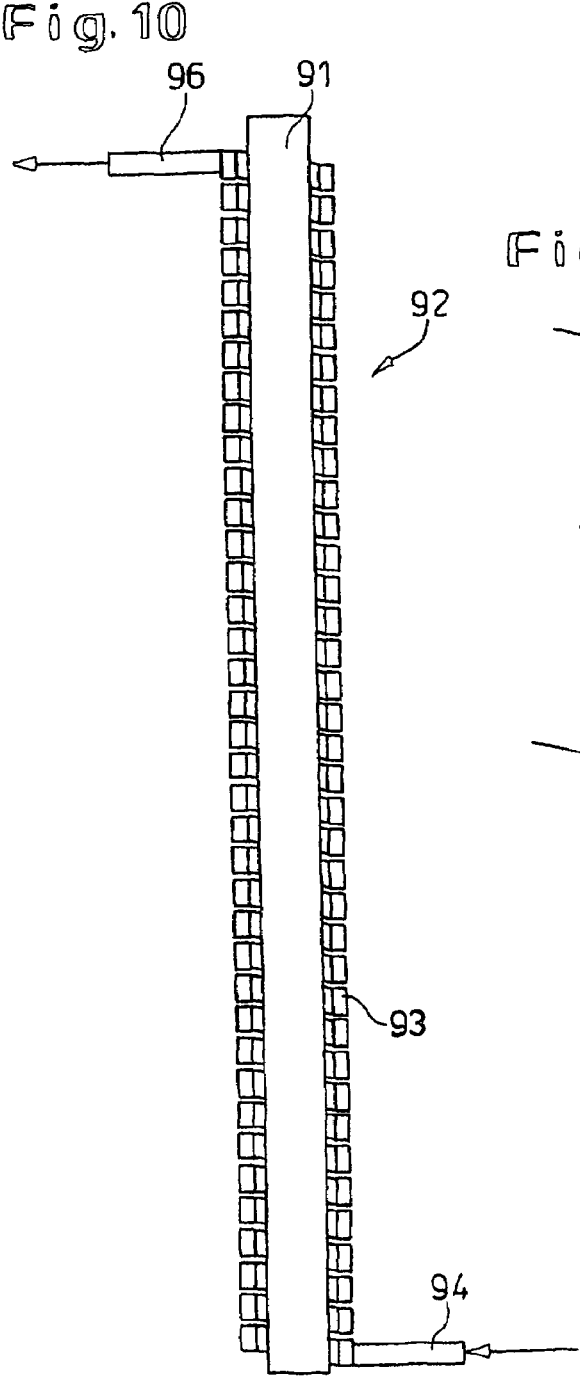
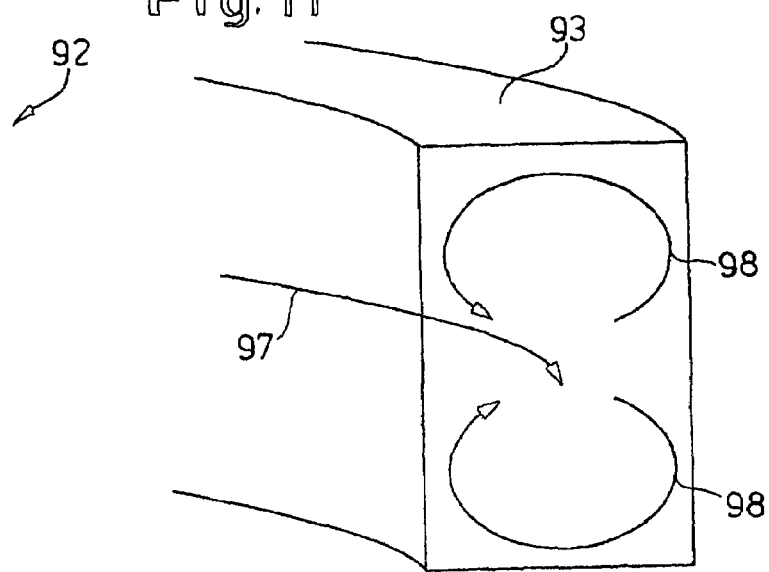

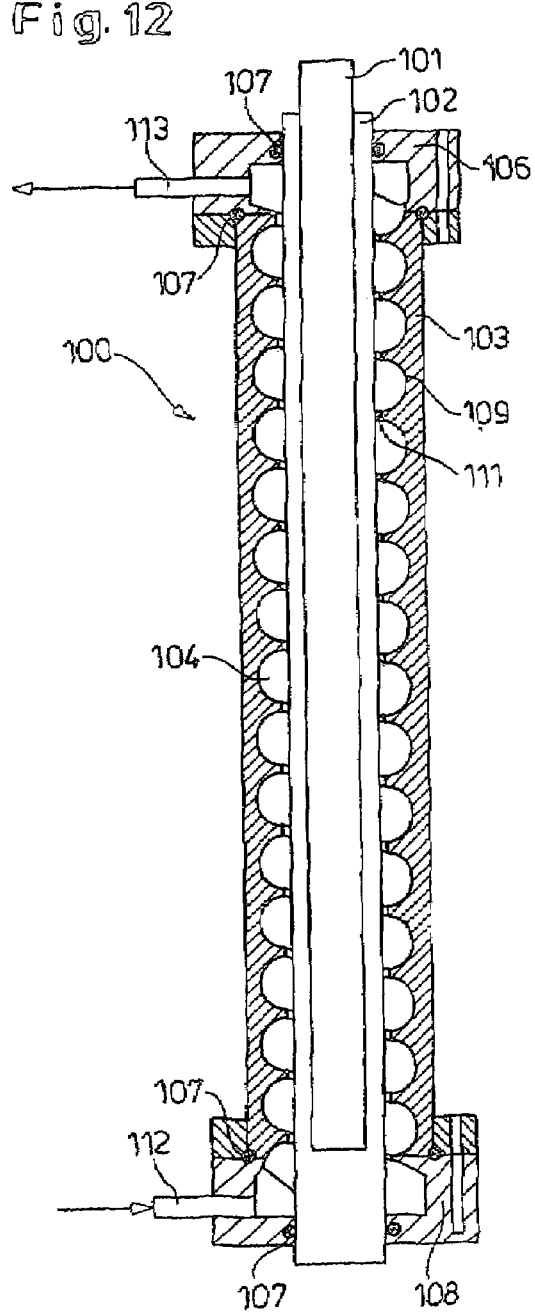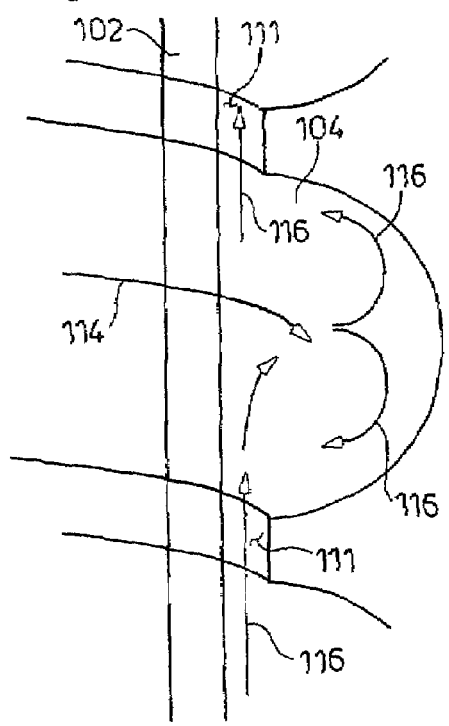

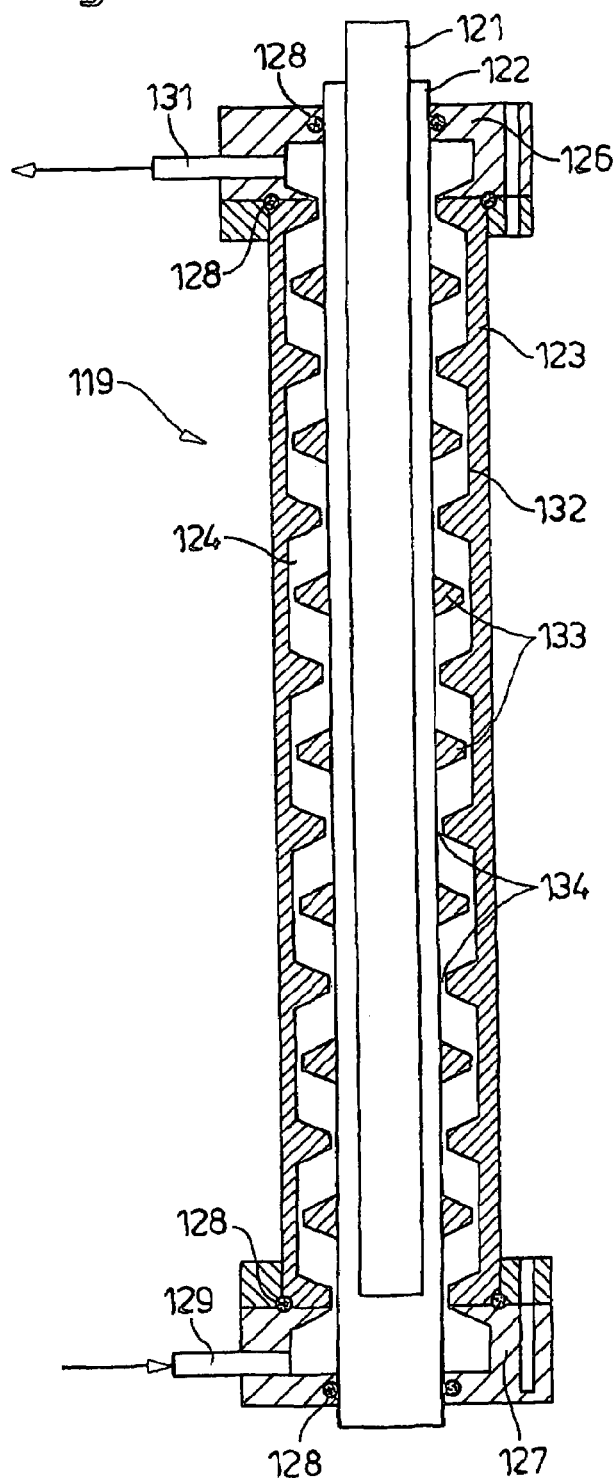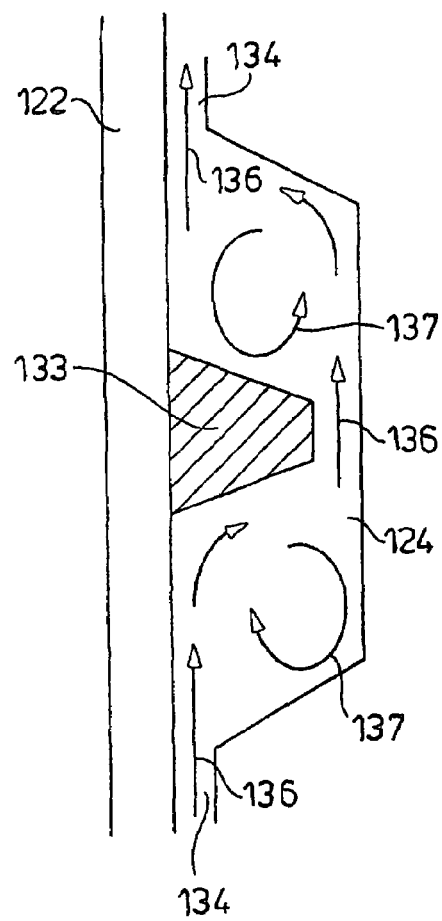

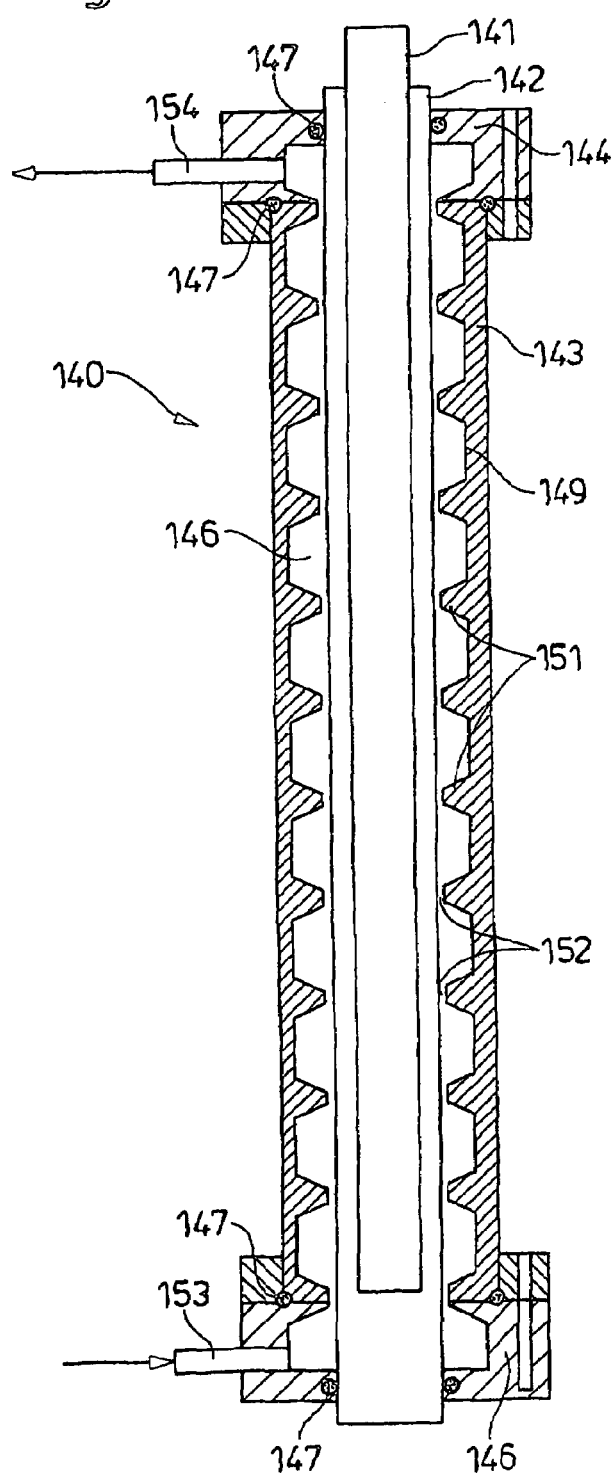
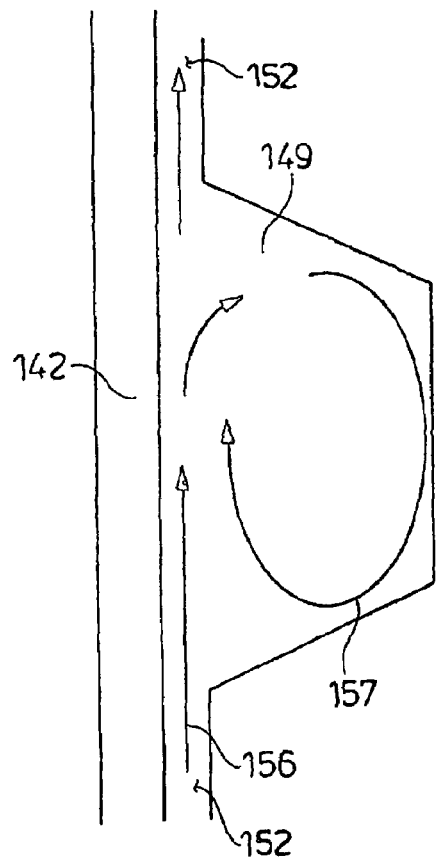

Fig. 18
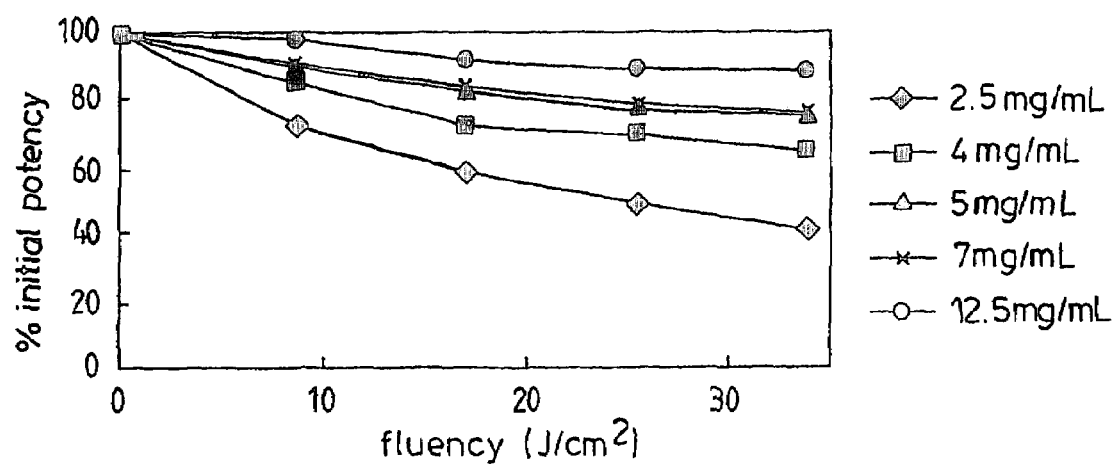
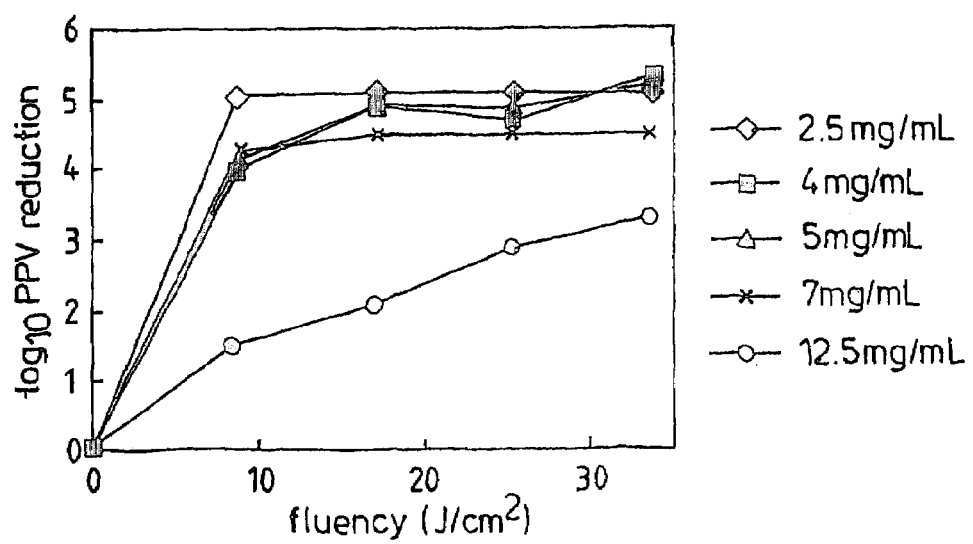

METHOD OF INACTIVATING MICROORGANISMS IN A FLUID USING ULTRAVIOLET RADIATION

RELATED APPLICATIONS

This application is a continuation of U.S. application Ser. No. 10/196,020, filed Jul. 16, 2002 now abandoned, the disclosure of which is incorporated by reference herein in its entirety, which is a continuation of U.S. application Ser. No. 09/711,780, filed Nov. 13, 2000, now abandoned.

FIELD OF THE INVENTION

The present invention relates generally to the sterilization of fluids such as biological fluids to inactivate undesired microorganisms such as viruses in the fluids. More specifically, the invention relates to sterilization of fluids by means of controlled ultraviolet irradiation.

BACKGROUND

Sterilization of fluids is an essential step in the manufacture of many pharmaceutical products and foodstuffs. Its goal is the reliable elimination of microorganisms, including viruses, while preserving, as intact as possible, the desirable components of the products. Sterilization may be required of biological fluids, such as nutrient media for fermentation, various blood products, and fluids bearing active pharmaceutical proteins. In the food industry, sterilization of fluid such as milk products is common.

In terms of food sterilization, the selection of a particular sterilization technique frequently is governed by how the procedure will affect the shelf life or the palatability of the food. While the greatest concern in the food industry is bacterial or fungal contamination, dairy products also may carry the additional risk of viral or prion contamination. Elimination or inactivation of such microorganisms is a prerequisite to commercial distribution of these products.

In contrast to the food industry, the choice and use of a sterilization technique in the pharmaceutical industry is subject to the strict demands and regulations imposed upon all pharmaceutical agents that are to be directly administered to an animal or human. There is particular concern about contamination of biological fluids such as pharmaceutical products by viruses, which may be co-isolated from a natural source or introduced during a biotechnological process. For the sterilization of pharmaceutical products, a multi-step process historically has been employed to inactivate, or remove, or reduce viral contaminants. Each step in the process is based on different operational principles to ensure a reduction in the viral load within a fluid preferably by at least four orders of magnitude while preserving the viability of proteins and other desirable components of the fluid.

Irradiation of biological and other fluids with ultraviolet (UV) light has been employed as a method for inactivating undesirable microorganisms. Irradiating plasma and blood products, for example, with UV-light to inactivate viruses was known during WW II. UV-treatment of blood derivatives is especially useful for treating uncoated, heat-stable viruses. Thus, Chin et al., Photochem. & Photobiol. 65, 432-435 (1997) teaches that irradiation of plasma products with UV-light leads to inactivation of the hepatitis A virus and parvoviruses.

UV-irradiation may inactivate microorganisms and/or viruses by generating mutagenic alteration of their genetic material. Above a minimum dose of radiation, the microorganisms lose their reproductive capacity. UV-irradiation damages nucleic acid by creating intrastrand nicks and inducing nucleotide photodimerization, both of which disrupt nucleic acid replication. Through such mechanisms, UV-irradiation can be an effective means of inactivating undesirable microorganisms within biological and other fluids. Unfortunately, the energy of short wavelength UV light also can damage sulfur-containing cysteine bridges and methionine peptide bonds and induce aromatic amino acid side reactions, thereby disrupting the structural and functional integrity of the very proteins that often are the desired end-products of the irradiated fluid. Thus, an inherent problem in the application of UV-irradiation techniques is controlling the irradiation of a fluid so as to ensure sufficient radiation exposure to inactivate undesirable microorganisms within a fluid while at the same time minimizing or eliminating UV-radiation damage to desirable proteins and other components within the fluid.

Traditionally, UV reactors have been used for the UV sterilization of biological fluids. Generally, a UV reactor includes a source of UV radiation such as, for example, one or more elongated tubular bulbs or lamps. In one configuration, an annular reaction chamber with a predetermined width is formed around and encloses the lamp and fluid to be irradiated is pumped or otherwise moved through the chamber, where it is exposed to UV light from the lamp. In another configuration, a UV source or sources may surround and radiate inwardly into a central tubular reaction chamber. In either case, flow rate, light intensity, chamber width or diameter, and reactor length are selected for a particular fluid to ensure, as much as possible, the most effective UV radiation dosage for deactivating undesirable microorganisms while conserving the viability of the desirable components of the fluid.

A problem with the use of UV reactors for irradiating fluid with ultraviolet light results from the finite width of the reaction chamber and the laminar nature of the fluid flow along the chamber. More specifically, as the fluid flows along the chamber, the UV radiation intensity in the treated fluid decreases relatively rapidly as a function of distance from the radiation source. This is due to many factors including the natural inverse-square law of radiation intensity as a function of distance from a source and the absorption characteristics of the fluid and the proteinaceous material supporting the infectious particles. In any event, microorganisms and viruses within layers of the fluid that flow along the outside of the reaction chamber farther from the radiation source receive no or a reduced dosage of radiation. These microorganisms are, therefore, inactivated slowly or not at all. On the other hand, microorganisms in layers of fluid that flow along the inside of the reaction chamber closest to the radiation source receive increased dosages, and in many cases overdoses, of radiation, which, in some cases, is high enough to cause significant damage to desirable proteins and other components in these layers of the fluid. The result is unpredictable and inefficient sterilization and higher levels of damage to desirable components.

Attempts to address these limitations have led to the development of thin-layer or thin film UV reactors in which the width of the reaction chamber and thus the thickness of the fluid layer adjacent the UV source is maintained relatively thin to reduce the detrimental effects of radiation intensity gradients in the fluid (see e.g. Kallenbach et al., Cur. Stud. Hematol. Blood Transfus. Basel 56, 70-82, (1989); Habel et al., J. Immunol. 56, 273-279(1947); Milzer et al., J. Immunol 50, 331-340 (1945). Oppenheimer et al., Am., J. Pub. Health. 49, 903-923, (1959)). The goal is to ensure that all of the fluid is constrained to a region of relatively smaller radiation intensity change as it moves along the radiation source. Thus, the difference in intensity at various layers within the fluid flow is theoretically controlled.

While thin-film reactors have been somewhat successful on a smaller scale, they are problematic in that they can only be scaled up to industrial production throughput with difficulty. This is because keeping the film thickness small and constant can only be realized by increasing the diameter of the reactor and thereby increasing the cross-sectional area of the film to accommodate the desired higher throughput. On an industrial scale, this necessary condition leads to unmanageably large reactors. One attempt to circumvent this problem is suggested in U.S. Pat. No. 5,133,932 which discloses a cylindrical thin-film UV-irradiation reactor in which the area of the film exposed to the UV-light is increased by corrugating the surfaces of the reaction chamber. However, the realized increase in throughput with such a device is marginal at best and still insufficient to accommodate large scale industrial production.

A further limitation of and problem with traditional UV-irradiation reactors is the unfavorable flow profile and dynamic conditions of fluid films when in laminar flow along the radiation source. More specifically, in a laminar flow there is no or very little fluid exchange normal to the flow direction. Thus, as mentioned above, fluid layers farther from the source receive a smaller radiation dose than fluid layers close to the source. Furthermore, the flow velocity profile within a confined laminar flow is such that the flow velocity is relatively low adjacent to the walls of the reaction chamber and is substantially higher intermediate the walls. Thus, fluid closest to the wall of the reaction chamber adjacent the light source flows more slowly and is exposed to the UV radiation substantially longer than fluid between the walls of the reaction chamber. Accordingly, to produce the minimum radiation dose necessary for inactivation of microbial contaminants in the most rapidly flowing fluid layers, the average residence time of the fluid in the reactor must be increased. This leads, however, to increased radiation dosage in the slower moving boundary layers of the fluid flow and consequent increased probability of undesired damage to desirable components in these layers. Thus, destruction of desirable components in the boundary layers due to overexposure is virtually inevitable.

One adverse result of overexposure in some layers of the fluid is the generation of free radicals, which become entrained in the flow and which have adverse effects on desirable components of the fluid. Attempts to minimize damage caused by free-radical generation as a result of overexposure typically include the use of free-radical scavengers in the fluid. Earlier studies have suggested that the use of free-radical scavengers can reduce indirect damage to proteins (Chin et al., Photochem. Photobiol. 65, 432 (1997). Chapman et al. in U.S. Pat. No. 5,922,278 discloses a UV-irradiation sterilization of biological fluids wherein free radicals are scavenged by a scavenging agent. Clark et al. in U.S. Pat. No. 5,786,598 discloses high intensity pulses of short wavelength light to deactivate microorganisms. Morgalis-Nunno et al., U.S. Pat. No. 6,087,141, discloses the use of light in the wavelength range of 340-400 nm (UVA) rather than short wavelengths of about 280 nm or less. Protection of the desired functionality of the fluid is afforded by adding a free-radical scavenger in the form of psoralen. Morowitz et al., U.S. Pat. No. 5,981,163 teaches the addition of quenching protective agents during irradiation deactivation of viruses. While such techniques attempt to deal with the free-radicals generated in the fluid, none address the problems, such as overexposure, that result in the formation of such free-radicals in the first place.

The disruption of the laminar fluid flow through UV reactors has been proposed as a solution to some of the forgoing problems. For example, tangential-flow ring-slot reactors have been proposed as a means to disrupt and induce mixing within the laminar flow layers of a UV reactor. EP 803472 A1 discloses a reactor for UV irradiation of a fluid having an annular or ring-slot reaction chamber surrounding a UV radiation source. The fluid inlet into the reaction chamber is orientated so that the fluid enters tangentially into the chamber in hopes of generating fluid cross-mixing. U.S. Pat. No. 5,433,738 discloses an irradiation reactor for the irradiation of water that includes a helical guide with circular cross section in hopes of generating fluid cross-mixing.

The tangential inflow solution has proven problematic in that the fluid flow through the reaction chamber rapidly reverts, due to wall friction and other hydrodynamic factors, to a fully axial and laminar profile directed along the longitudinal axis of the chamber. The Dean vortices, which are theoretically postulated at least for the area of tangential inflow, and which are intended to promote cross-exchange of the reaction medium within the reaction chamber, are surprisingly not present according to visual studies and CFD-investigations (flow simulation). Tangential entry ring-slot reactors, therefore, afford only a limited solution to the problems discussed above.

A need therefore exists for a method of sterilizing a fluid such as a biological fluid with UV radiation that ensures adequate exposure to inactivate undesirable microorganisms, while simultaneously minimizing or eliminating damage to desirable components in the fluid.

A further need exists for an improved method of inactivating microorganisms in a fluid reaction medium with UV radiation that eliminates the need to use free radical scavenging or quenching agents.

There is also a need for a method of sterilizing biological fluids that is effective at deactivating undesirable microorganisms while preserving the viability of desirable components without the use of scavengers and that is scalable to commercially viable production throughput.

It is to the provision of a method that addresses these and additional needs that the present invention is primarily directed.

SUMMARY OF THE INVENTION

Briefly described, the present invention is a method of inactivating microorganisms such as viruses suspended in a fluid by irradiating the fluid with UV light. The method can be applied to the sterilization of biological products and foodstuffs, including, but not limited to, blood components, fermentation media from recombinant technology, milk and milk products, drinking water, fruit juices and other beverages like soft drinks, chemical and pharmaceutical products, virus vaccines, genetically produced drugs and proteins, drugs and proteins from transgenic animals and plants, and blood plasma and products from blood plasma. In a best mode of carrying out the invention, UV exposure is achieved in a generally tubular reactor wherein the fluid flows through a reaction chamber that surrounds an elongated tubular UV light source.

In general, the method comprises the steps of establishing a primary flow of the fluid in a first direction along the radiating surface of a UV light source and superimposing on the primary flow a circulating secondary flow of the fluid. The secondary flow circulates in a direction substantially transverse to the radiating surface of the UV source such that the entire volume of the fluid circulates repeatedly toward and away from the UV source as the primary flow carries it along the length of the source. As a result, all of the fluid receives a constant average dosage of UV radiation and the problems previously associated with laminar flows in UV reactors, namely overexposure near the radiating surface and underexposure farther from the radiating surface, are eliminated.

Further, and in direct contrast to thin-film reactors, the reaction chamber in a reactor for carrying out the method of the present invention may be much wider than an effective "kill zone" immediately adjacent the radiating surface of the UV light source wherein the intensity of the radiation is always above the inactivation threshold. This is because, as the fluid circulates toward and away from the source in the circulating secondary flow, all of the fluid moves successively into and out of the kill zone adjacent the surface of the source. The average residence time of the fluid in the kill zone and thus the radiation dosage received is a function, among other things, of the thickness of the kill zone in the particular fluid being treated, the intensity of the UV light source, and the characteristics of the primary and secondary flows. Significantly, these parameters can be controlled as needed, according to the invention, to establish and maintain an average kill zone residence time for the entire volume of fluid that corresponds to a predetermined required dosage of UV radiation.

Further, since the reaction chamber can be much wider than in thin-film reactors, reasonably sized high volume reactors that are scalable to commercial production throughputs are possible. Finally, since the average radiation dosage received by all of the fluid is constant, i.e. no portions or layers of the fluid are overexposed and none are underexposed, the formation of free-radicals common in prior art UV reactors is virtually eliminated. Thus, the method of the invention can be used to sterilize biological or other fluids without the need to use free-radical scavengers.

The methodology of the invention, including the establishment and maintenance of a circulating secondary flow superimposed on a primary flow, can be realized through a variety of reactor and reaction chamber configurations. Several such configurations are discussed in some depth in the detailed description set forth. It will be understood, however, that the method of the invention might well be carried out by other reactor designs and configurations, but that the essence of the methodology of the invention is substantially the same. Regardless of the design of the apparatus for establishing and maintaining the conditions of the invention, the method has been demonstrated to provide controllable and predictable inactivation with minimum damage to desirable components, without the need for free-radical scavengers, and with the potential for commercially viable throughput. Additional objects, features, and advantages of the invention will become more apparent upon review of the detailed description set forth below when taken in conjunction with the accompanying drawing figures, which are briefly described as follows.

BRIEF DESCRIPTION OF THE DRAWINGS

FIGS. 10 and 11 are sectional views illustrating another alternate embodiment of a UV reactor usable for carrying out the methodology of the present invention.

FIGS. 12 and 13 are sectional views illustrating still another alternate embodiment of a UV reactor usable for carrying out the methodology of the present invention.

FIGS. 14 and 15 are sectional views illustrating still another alternate embodiment of a UV reactor usable for carrying out the methodology of the present invention.

FIGS. 16 and 17 are sectional views illustrating yet another alternate embodiment of a UV reactor usable for carrying out the methodology of the present invention.

FIG. 18 presents two graphs showing $\alpha_1$PI potency and porcine parvovirus (PPV) reduction as a function of fluency at various $\alpha_1$PI concentrations and illustrates the determination of critical parameters in accessing UV sterilization methodologies.

FIG. 21 shows the results of experiment 4.

DETAILED DESCRIPTION OF THE PREFERRED EMBODIMENTS

Figure 1:
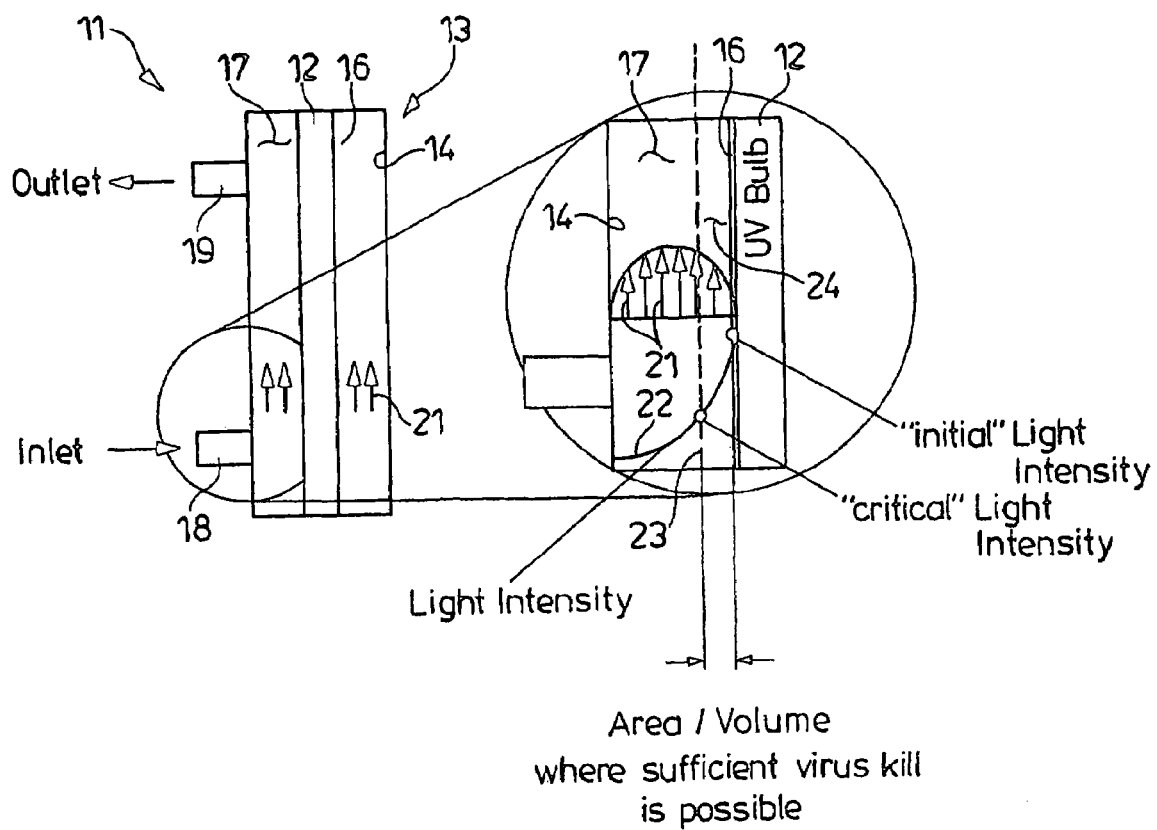
FIG. 1 is a simplified schematic representation of a typical ring-slot UV reactor illustrating the characteristics of a laminar fluid flow.

Referring now in more detail to the drawings, wherein like numerals refer where appropriate to like parts throughout the several views, FIG. 1 illustrates general principles of fluid flow through a traditional prior art tubular or ring-slot UV reactor and the problems and shortcomings associated therewith. The reactor 11, which is shown in simplified schematic form for clarity, includes an ultraviolet radiation source in the form of a centrally disposed elongated tubular UV lamp 12. The UV lamp 12 is surrounded by a cylindrical housing 13 having an outer wall 14 and an inner wall 16, which bound and define an annular or ring shaped reaction chamber 17 surrounding the lamp 12. The inner wall 16 of the housing is transparent to ultraviolet radiation such that UV light from the lamp 12 radiates into the reaction chamber 17. The reaction chamber 17 has a predetermined width defined by the distance between its outer and inner walls 14 and 16 respectively. A fluid inlet port 18 communicates with the reaction chamber 17 at one end, the bottom end in FIG. 1, and a fluid outlet port communicates with the reaction chamber 17 at the opposite end, the top end in FIG. 1.

Fluid to be sterilized is pumped or otherwise fed to the fluid inlet port 18 and flows upwardly through the reaction chamber 17 and along the length of the UV lamp as indicated by arrows 21 before exiting the reaction chamber through fluid outlet port 19. As the fluid moves through the reaction chamber, it is exposed to UV radiation from the UV lamp 12, which acts to sterilize the fluid by inactivating undesirable components in the fluid. In the case of the inactivation of viruses within a biological fluids such as blood products, for example, the UV radiation theoretically inactivates or "kills" the virus particles within the fluid as the fluid flows through the reaction chamber.

The enlarged inset in FIG. 1 depicts in more detail the fluid flow pattern through the reaction chamber 17 and its relationship to the UV radiation intensity profile in the chamber and also illustrates a fundamental cause of problems with prior art reactors and UV inactivation techniques. More specifically, the fluid moves through the reaction chamber and along the length of the UV lamp 12 in a substantially laminar flow, meaning that there is little if any fluid movement in a direction transverse to the lamp. In other words, fluid layers within the reaction chamber tend to retain their relative distances from the UV lamp as the fluid moves along the entire length of the chamber. Thus, fluid layers near the outer wall 14 tend to stay near the outer wall and fluid layers near the inner wall 16 tend to stay near the inner wall. Furthermore, as is true of confined laminar flows in general, the boundary layers of fluid near the inner and outer walls of the chamber move more slowly than fluid layers intermediate the walls, as illustrated by the velocity profile arrows 21 in FIG. 1. Thus, the residence time in the reaction chamber of fluid in the boundary layers is greater than the residence time of fluid in intermediate layers of the flow.

Curve 22 represents the radiation or light intensity within the reaction chamber 17 as a function of distance from the UV lamp 12. The initial intensity immediately adjacent the UV lamp is relatively high and essentially is the inherent surface intensity of the lamp itself. However, as discussed in some detail above, the light intensity falls off rapidly as a function of distance from the lamp due to a variety of factors including the natural inverse square law of radiation intensity and the light absorption characteristics of the fluid. At some threshold distance from the lamp, indicated at 23 in FIG. 1, the light intensity is equal to a "critical" intensity, below which UV radiation levels are insufficient to inactivate viruses within the fluid. This critical distance defines the outer boundary of a "kill zone" 24 within which viral inactivation occurs and outside of which viruses within the fluid are substantially unaffected by the UV radiation. It will thus be seen that with a traditional laminar fluid flow through the reaction chamber 17, layers of fluid within the kill zone are sterilized while layers of fluid outside the kill zone pass through the reactor without being sterilized. As a result, reduction of viral load in such a reactor is subject to natural limits imposed by the fact that only a portion of the fluid is affected by the UV radiation.

In an attempt to address this problem, thin-film reactors have been developed wherein the width of the reaction chamber itself is equal to or less than the width of the kill zone. The theory is that with such a reactor, all of the fluid necessarily will reside in the kill zone as it moves through the reactor and thus will be subjected to sufficient doses of radiation to affect sterilization. However, as mentioned above, such thin-film reactors cannot be scaled up to accommodate commercially viable fluid throughputs with a reasonably sized reactor. Furthermore, even if practical upscaling were possible, a problem still exists with thin-film reactors because of the fundamental laminar character of fluid flow and the nature of the flow velocity profile across the width of the reaction chamber. More specifically, even in a thin-film reactor, layers of fluid adjacent the UV source are exposed to substantially higher doses of radiation than layers of fluid at the outer boundary of the reaction chamber. Furthermore, because of the flow velocity profile of a confined laminar flow, layers of fluid adjacent the UV source also experience a longer residence time within the reaction chamber than layers of fluid intermediate the walls of the chamber. As a consequence of these conditions, fluid layers adjacent the UV source tend to be overexposed, which results in a relatively high instance of damage to desirable components such as proteins. The overexposure increases the likelihood of the presence of free radicals within the fluid, which themselves can result in further destruction of desirable components of the fluid. Although the use of free radical scavengers is commonly taught as a solution to this later problem, this represents only an after-the-fact patch rather than a solution and decreases the efficiency of the sterilization process.

Figure 2:
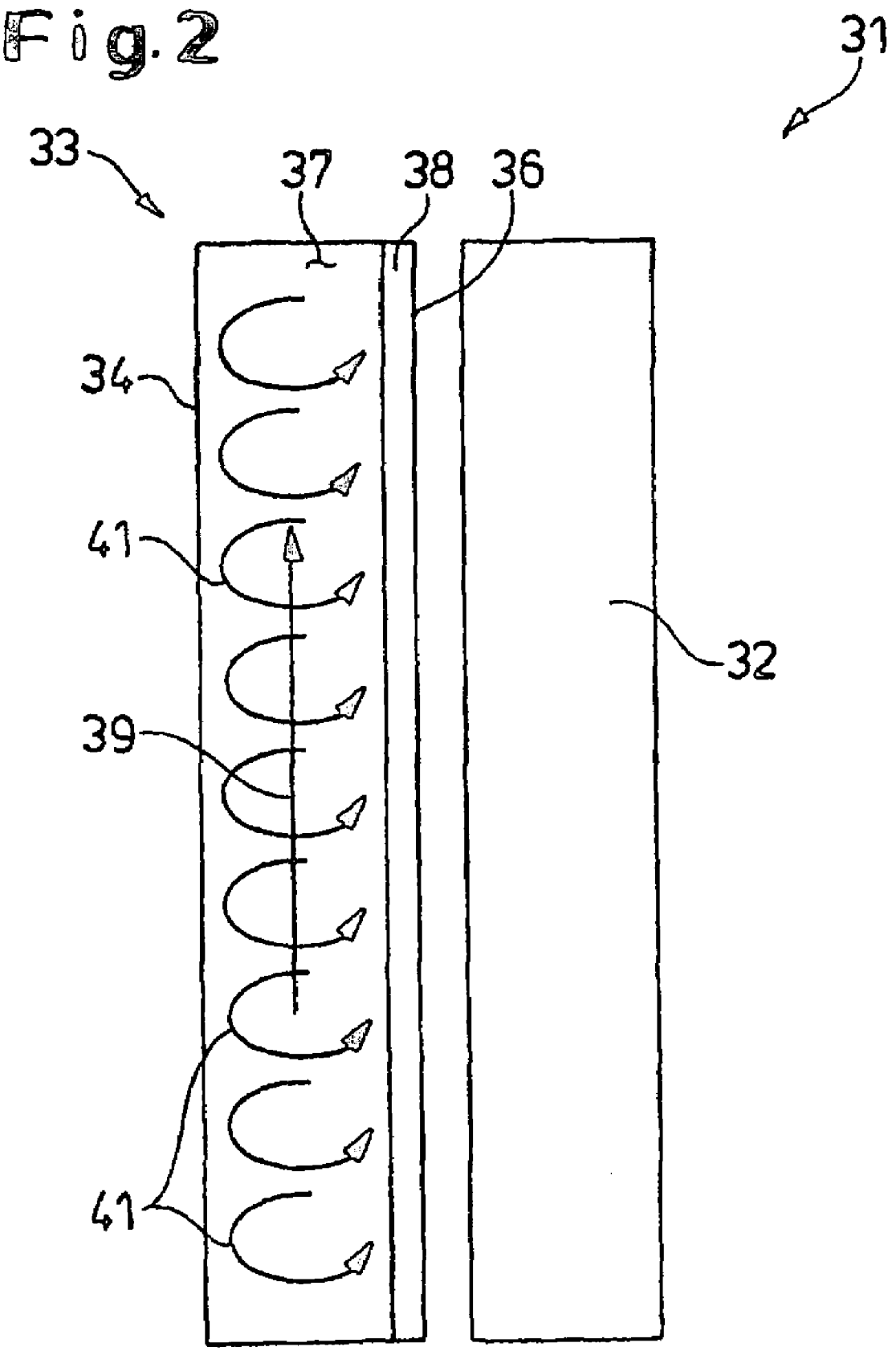
FIG. 2 a simplified cross-sectional view of a portion of a UV reactor illustrating fundamental principles of the present invention.

With the forgoing background in mind, FIG. 2 illustrates, in simplified schematic form, the unique methodology of the present invention for addressing and eliminating the problems that plague prior art UV reactors, including thin-film reactors. The invention is illustrated in FIG. 2 within the context of a simplified UV reactor 31 having an axially extending UV lamp 32 adapted to radiate ultraviolet radiation in a predetermined frequency band. In the preferred embodiment, the lamp 32 radiates UVC radiation; that is, radiation having a wavelength between about 180 and 320 nm, or more preferably between about 225 and 290 nm, and most preferably about 254 nm. UVC radiation is preferred because it tends to cause less detrimental effects on desirable components such as proteins within a fluid being treated while retaining sufficient energy to inactivate viruses and other target microorganisms within the fluid. However, other types of UV radiation such as, for example, UVA and UVB are contemplated and are within the scope of the invention.

The UV lamp 32 is disposed along the central axis of a generally tubular housing 33 having an outer wall 34 and an inner wall 36 that bound and define an elongated annular reaction chamber 37. Obviously, the inner wall 36 of the housing is transparent to UV radiation so that UV light from the lamp 32 radiates into the chamber 37. A fluid, such as a biological fluid, to be treated is pumped or otherwise moved through the annular reaction chamber 37 by an appropriate pump (not shown) so that the fluid progresses (in the embodiment of FIG. 1) from the bottom of the reaction chamber toward the top of the reaction chamber, where it exits the chamber through an outlet port (not shown). Generally speaking, as the fluid moves through the reaction chamber 37 and along the length of the UV lamp 32, it is irradiated with UV radiation from the UV source to inactivate microorganisms such as viruses contained within the fluid.

As discussed above, an inactivation or kill zone 38 is defined along the inner wall 36 of the reaction chamber. The width of the kill zone is determined by many factors including the intensity of the lamp, the composition and optical characteristics of the fluid, and others; but generally represents the zone within which the intensity of UV radiation is above a threshold required to affect inactivation of microorganisms within the fluid. Outside the kill zone 38, the radiation intensity generally is to low to affect inactivation and this is the phenomenon that in the past has led to the development of thin-film reactors as discussed above.

In the method of the present invention the fluid to be treated is moved in a primary flow 39 along the length of the reaction chamber 37 and thus along the surface of the UV lamp 32 as expected. However, and unlike prior art methods, a circulating secondary flow 41 is established within the fluid and is superimposed on the primary flow 39. The circulating secondary flow 41 preferably is generally radially or transversely relative to the surface of the UV lamp. Thus, as the fluid moves along the UV lamp in the general direction of the primary flow 39, it also circulates repeatedly from the outer wall 34 toward the inner wall 36 of the reaction chamber and back again in the circulating secondary flow 41. As a consequence, the fluid moves repeatedly from a region in the reaction chamber outside the kill zone 38, into and through the kill zone 38 to the inner wall 36 of the reaction chamber, and thence away from the inner wall, back through the kill zone, and back into the region outside the kill zone.

Imagine for a moment a droplet or particle of fluid entrained within the fluid flowing through the reaction chamber. The droplet may contain undesirable microorganisms such as viruses as well as desirable components such as proteins. As the droplet moves generally along the length of the reaction chamber in the direction of the primary flow 39, it also circulates repeatedly with the superimposed secondary flow first across the border of the kill zone where it receives the threshold radiation intensity, then through the kill zone 38 where it receives progressively increasing radiation intensity until it reaches the inner wall 37 of the reaction chamber, where it receives the maximum radiation intensity. From the inner wall, the imaginary droplet continues to move with the secondary flow away from the inner wall 36 and back through the kill zone 38, receiving progressively less radiation intensity, until it moves out of the kill zone and into the inactive region of the reaction chamber outside the kill zone.

From the forgoing, it will be appreciated by skilled artisans that, in each cycle through the kill zone, the imaginary droplet of fluid experiences an average intensity or dosage of UV radiation that is greater than the threshold intensity at the boundary of the kill zone 38 and less than the maximum intensity at the inner wall 36 of the kill zone. The total radiation "seen" by the droplet during its residence in the reaction chamber is therefore approximately equal to the average radiation experienced in each cycle times the number of repetitive cycles within the circulating secondary flow 41. The beneficial result is that each droplet of the fluid, or, in other words, the entire volume of fluid, experiences a constant average dosage of UV radiation as it moves through the reaction chamber. Further, the dosage itself can be controlled relatively easily by controlling the intensity of the UV lamp 32, which effects the width of the kill zone, and the characteristics of the primary flow 39 and the superimposed circulating secondary flow 41. Therefore, not only is the entire fluid exposed to a constant average dosage of radiation, but the dosage is controllable and may be adjusted to achieve optimum inactivation of undesirable microorganisms while preserving as intact as possible the desirable components within the fluid.

The methodology of the invention as illustrated in FIG. 2 contrasts starkly with the processes within prior art laminar flow UV reactors where, as mentioned above, fluid layers adjacent the inner wall of the reaction chamber tend to be over-irradiated resulting in unwanted damage to desirable components and the creation of free radicals, while layers farthest from the inner wall tend to be under-irradiated resulting in low microorganism inactivation rates. Thus, it has been found that, with the method of the present invention, high inactivation rates, on the order of four orders of magnitude or more in viral inactivation of biological fluids, can be obtained and consistently maintained. Further, this level of inactivation is achieved without the need to introduce free radical scavengers into the fluid. This is because fewer free radicals are created when practicing the method of the invention since no portion of the fluid is over-irradiated as is the case in prior art UV reactors. Finally, and significantly, since the circulating secondary flow of the present methodology repeatedly moves into and out of the kill zone regardless of the total width of the reaction chamber, the constraints that previously gave rise to the development of thin-film reactors simply are not present. Thus, the reaction chamber in a reactor for carrying out the invention may be significantly wider than the thickness of the kill zone itself, making such a reactor easily scalable to commercial production throughput while maintaining a reactor of reasonable size. It will thus be seen that the present invention offers many significant advantages over prior art UV inactivation methods and devices.

The methodology of the present invention will now be described within the context of several exemplary reactor configurations usable for carrying out the invention as it has generally been described above. It will be appreciated, however, that the invention is not limited to or constrained by the illustrated reactor configurations, but that such are offered to facilitate a better understanding of the invention and to provide an enabling disclosure for its practice.

Figure 3:
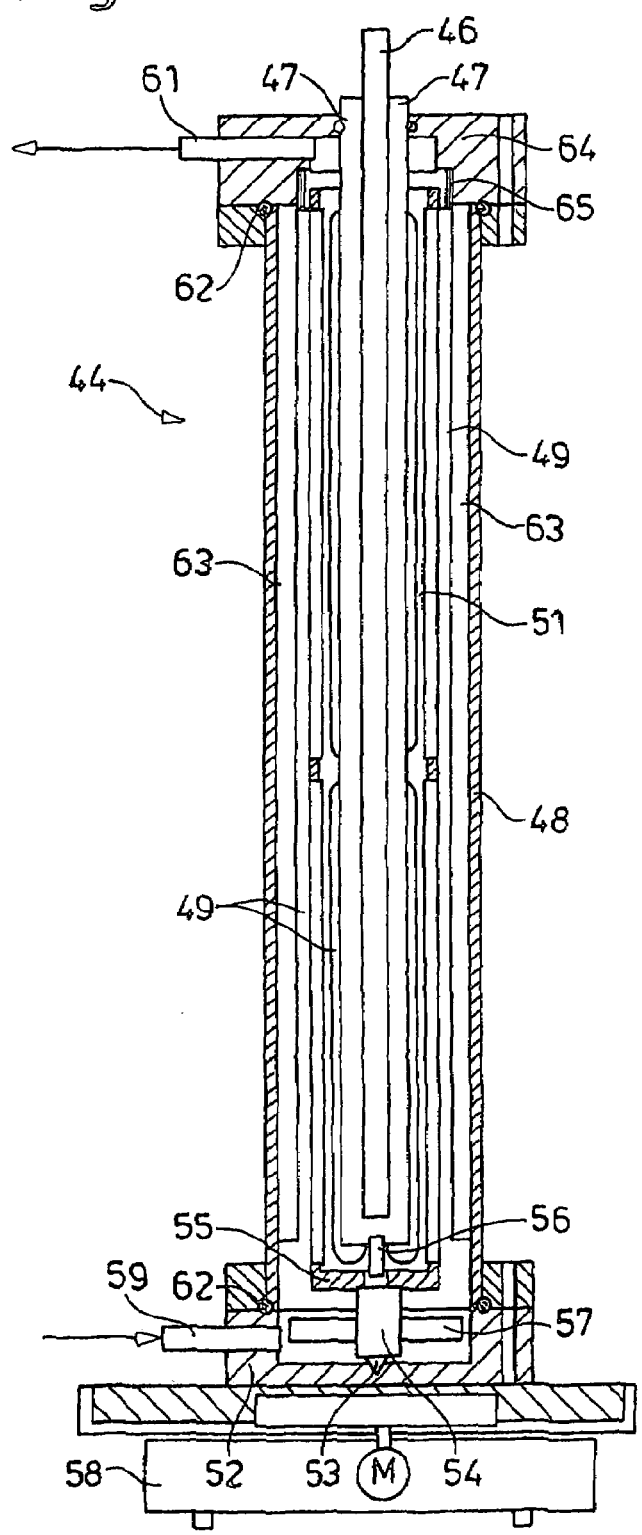
FIGS. 3 through 7 are sectional views illustrating one embodiment of a UV reactor with rotating agitator usable for carrying out the methodology of the present invention.
Figure 4:
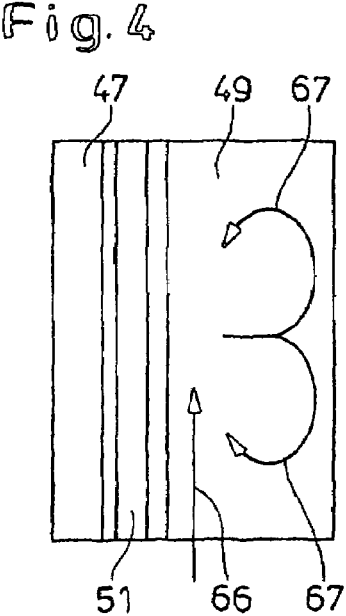
Figure 5:
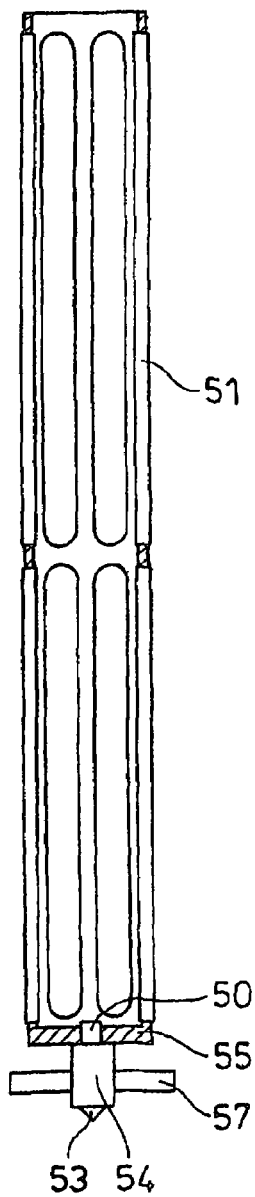

FIGS. 3 through 5 illustrate a rotating agitator reactor usable for carrying out the method of the invention. The reactor includes an axially disposed elongated UV lamp 46 disposed within a glass mantle or inner housing 47. A tubular housing 48 surrounds the glass mantle 47 and a reaction chamber 49 through which fluid may flow is defined between the inner wall of the tubular housing and the glass mantle. The housing is capped and sealed at its top end by a head cover 64 and associated O-rings 62 and at its bottom end with a base cover 52 and associated O-rings 62. An inlet port 59 communicates with the bottom portion of the reaction chamber 49 for introduction of fluid into the reaction chamber and an outlet port 61 communicates with the top portion of the reaction chamber for egress of fluid therefrom.

A rotatable anchor agitator 51 is disposed within the reaction chamber surrounding the glass mantle 47 and is formed with from about 4 to about 10, and preferably about 8, vanes that surround the glass mantle 47. The anchor agitator 51 is rotatably journaled at its top end in a sleeve bearing 65 and is rotatable supported and centered at its bottom end on an agitator shaft 54 that terminates in a tapered centering tip 53. The centering tip 53 sits and rides in an appropriately shaped depression in the bottom of the base cover 52 so that the anchor agitator is rotatable about the glass mantle 47 in such a way that its vanes repeatedly circle the glass mantle within the reaction chamber 49.

A diametrically extending magnetic coupler arm 57 is attached to the agitator shaft and is adapted to couple magnetically with the magnetic coupler of a magnetic drive 58. It will be appreciated that activation of the magnetic drive 58 causes the anchor agitator 51 to rotate within the reaction chamber 49. A centering pin 56 depends from the bottom of the glass mantle 47 and is disposed in a corresponding seat in the bottom 55 of the anchor agitator 51 to keep the mantle centered with respect to the anchor agitator and to maintain the relatively small clearance between the vanes of the agitator and the surface of the glass mantle. Preferably, but not necessarily, an array of inwardly projecting flow breakers 63 are disposed around the inner wall of the housing 48.

FIG. 4 illustrates use of the reactor 44 to carry out the methodology of the present invention. Fluid to be irradiated is pumped through the inlet port 59 and exits out the outlet port 61 establishing a primary flow 66 along the length of the UV lamp 46. Thus, as the fluid flows upwardly along the length of the reaction chamber 49, it is exposed to UV radiation through the glass mantle 47. At the same time, the anchor agitator 51 is rotated to move its vanes around the glass mantle 47. The movement of the agitator establishes a circulating secondary flow 67 of fluid that has a major component oriented in a direction transverse to the UV lamp 47. The flow breakers 63 have been shown to weaken the tendency of the secondary flow to establish tangential components in favor of a more transverse or radial flow direction. Thus, the fluid moves repeatedly toward and away from the UV source in the circulating secondary flows 67 as it progresses along the length of the reaction chamber with the primary flow to realize the benefits of the invention as discussed above. Agitator rotation rate, lamp intensity, and flow rate are all adjustable to obtain optimum irradiation for a given fluid being treated in the reactor.

Figure 6:
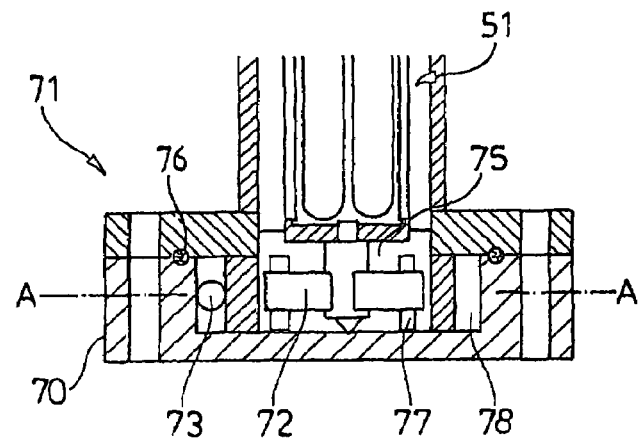
Figure 7:
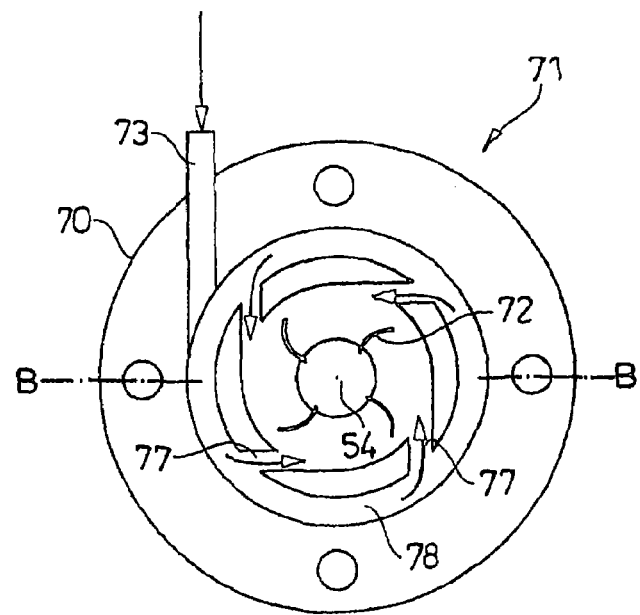

FIGS. 6 and 7 illustrate an alternative drive mechanism for the anchor agitator of FIGS. 3 through 5. The sealless drive mechanism 71 includes a drive housing 70 defining an internal cylindrical impeller chamber 75 and an outer annular channel 78. An array of tangentially oriented slots 77 communicate between the outer channel 78 and the impeller chamber 75. An inlet port 73 communicates with the outer channel 78 and is oriented to direct fluid tangentially into the outer channel as shown. With this configuration, fluid moves around the outer channel and enters the impeller chamber in a generally tangential direction as indicated by the arrows in FIG. 7.

The stirrer shaft 54 of the anchor agitator 51 rests on its tapered end in a corresponding depression in the bottom of the drive housing 70 such that the anchor agitator is rotatable within the reactor as described above. An array of arcuate vanes 72 project outwardly from the stirrer shaft 54 into the impeller chamber 75 and together form an impeller.

As fluid to be treated moves tangentially into the outer channel 78 and tangentially into the impeller chamber 75 through slots 77, the fluid impinges the vanes 72, which imparts rotary motion to the shaft 54, thus causing the anchor agitator 51 to rotate. Since the motion of the fluid itself causes the rotation of the anchor agitator, no ancillary drive mechanism, such as the magnetic drive of FIG. 3, is required. As the fluid moves out of the impeller chamber and into and through the reaction chamber of the reactor, the rotating anchor agitator causes circulating secondary flows superimposed on the primary flow as described above relative to FIGS. 3 and 4.

Figure 8:
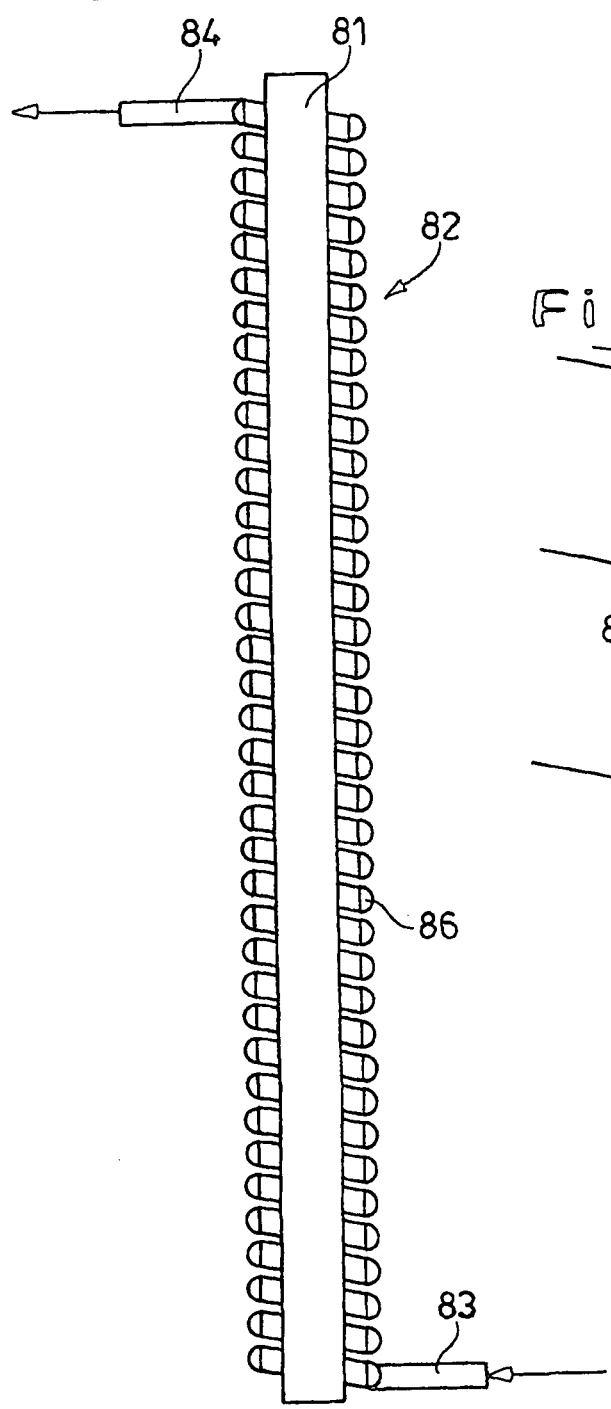
FIGS. 8 and 9 are sectional views illustrating an alternate embodiment of a UV reactor usable for carrying out the methodology of the present invention.
Figure 9:
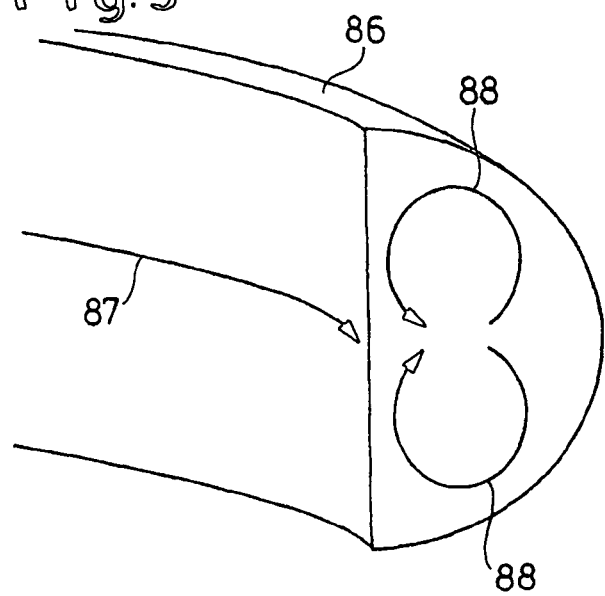

FIGS. 8 and 9 illustrate an alternate embodiment of a UV reactor usable to carry out the methodology of the present invention. An elongated UV lamp 81 is surrounded by a UV transparent (preferably quartz) spiral wound flow tube 82 defining a plurality of individual windings 86. The spiral wound tube 82 terminates at its bottom end in an inlet port 83 that communicates with the bottom end of the tube 82 and at its top end in an outlet port 84 that communicates with the top end of the tube 82. As indicated by the arrows in FIG. 8, fluid to be treated is pumped into the inlet port 83 and thence moves through the spiral wound tube 82 around and around the UV lamp 81, where it is exposed to UV radiation from the lamp.

As best illustrated in FIG. 9, the windings 86 of the tube 82 are formed with a generally D-shaped cross section having a generally rectilinear or flat surface adjacent the UV lamp and a curved outer surface. As the fluid flows through the tube in the general direction of a primary flow 87, the combination of surface tension, wall friction, and the greater distance that the fluid must transverse around the outer portion of the tube results in the formation of circulating secondary flows 88, also known as Dean vortices, within the tube. The circulating secondary flows 88 generally are oriented transversely with respect to and are superimposed on the primary flow, and thus are oriented generally transversely with respect to the UV lamp 81.

Thus, as the fluid moves along the surface of the UV lamp in the primary flow direction, the circulating secondary flows carry the fluid toward and away from the UV source according to the methodology of the invention with the many benefits described above. Obviously, an advantage to the reactor configuration of FIGS. 8 and 9 is that it contains no moving parts or drive mechanisms. The characteristics of the primary and secondary flows 87 and 88 respectively, and thus the UV radiation dosage experienced by the fluid, may be controlled by controlling, where feasible, the viscosity of the fluid, the dimensions of the spiral wound tube 82, and the flow rate of the fluid through the tube.

FIGS. 10 and 11 illustrate a UV reactor configuration similar to that of FIGS. 8 and 9, but with the spiral wound flow tube of the reactor having a generally rectangular rather than a D-shaped cross section. The elongated UV lamp 91 is disposed in and surrounded by a spiral wound quartz tube 92 defining a plurality of individual windings 93. An inlet port 94 communicates with the flow tube 92 at its bottom end and an outlet port 96 communicates with the flow tube 92 at its top end. Fluid to be treated is pumped into the inlet port and moves through the spiral wound tube 92 and thus in a spiral pattern along the surface of the UV lamp in the direction of a primary flow 97 (FIG. 11), and is exposed to UV radiation.

As with the embodiment of FIGS. 8 and 9, the surface tension, friction, and path length gradients within the tube 92 combine to create Dean vortices that manifest themselves as circulating secondary flows 98 superimposed on the primary flow 97. The circulating secondary flows 98 are oriented substantially transversely relative to the UV lamp and thus carry the fluid toward and away from the lamp according to the methodology of the invention and with the aforementioned benefits thereof. Again, radiation dosage is controllable by controlling fluid characteristics, lamp intensity, and flow rate through the reactor.

FIGS. 12 and 13 illustrate still another UV reactor configuration usable to carry out the methodology of the present invention. The reactor 100 includes an elongated UV lamp 101 disposed within a tubular quartz (or other UV transparent material) inner tube 102. An outer housing 103 surrounds the quartz tube 102 and, in conjunction therewith, defines a reaction chamber 102 extending along the length of the UV lamp 101. The housing 103 is capped at its top end by a head cap 106 and at its bottom end with a base cap 108, each of which is sealed to the housing 103 and quartz tube 102 with appropriate O-ring seals 107.

The inner surface of the housing 103 is machined to define a generally helical channel 109 that spirals continuously around the quartz tube 102 from the bottom of the reactor to the top. The helical channel approaches but does not engage the quartz tube 102 and thus defines a series of relatively narrow passages 111 between each turn of the helical channel and the quartz tube 102. An inlet port 112 communicates with the reaction chamber 104 at the bottom of the reactor and an outlet port 113 communicates with the reaction chamber 104 at the top of the reactor.

In use to carry out the methodology of the present invention, fluid to be treated is pumped into the reactor through the inlet port and flows generally around the helical channel and along the surface of the UV lamp in a primary flow 114. This motion of the primary flow generates circulating secondary flows 116 in the form of Dean vortices as a result of fluid dynamical interactions within the D-shaped channel. The circulating secondary flows 116 are superimposed on the primary flow 114 and carry the fluid toward and away from UV source according to the methodology of the present invention.

At the same time, the spaces 111 permit a small volume of the fluid to flow longitudinally along the length of the reactor in a free jet flow 116 (FIG. 13). The fluid in the free jet flow 116 is directed almost perpendicularly onto the spiraling primary flow 114. The interaction between the two flows causes an enhancement of the circulating motion of the secondary flows 116 as a result of the fluid dynamical forces generated by the interacting flows. This, in turn, leads to an improved and more even irradiation of the fluid as it moves through the reactor. UV irradiation dosage can be adjusted and controlled by controlling the dimensions of the helical channel, the size of the spaces 111, the viscosity of the fluid, the intensity of the lamp 101 and the fluid flow rates through the reactor.

FIGS. 14 and 15 illustrate yet another embodiment of a UV reactor usable to carry out the methodology of the present invention. The reactor 119 is similar in some respects to the reactor of FIGS. 12 and 13 and includes an elongated UV lamp 121 surrounded by a quartz tube 122. An outer housing 123 surrounds the quartz tube 122 and in conjunction therewith defines a reaction chamber 124 that extends along the length of the UV lamp 122. The housing is capped at its top end by a head cap 126 and its bottom end by a base cap 127, each of which is sealed to the housing and the quartz tube with appropriate O-rings 128. An inlet port 129 communicates with the reaction chamber at the bottom thereof and an outlet port communicates with the reaction chamber at its top end.

The inner wall of the housing 123 is machined or otherwise formed with a series of generally annular channels 132 separated by inward protrusions 135. The inward protrusions 135 approach but do not touch the quartz tube, thus defining relatively narrow passages 134 between the channels 132. An array of generally ring-shaped baffles 133 project outwardly from the quartz tube 122 with each baffle being disposed within a corresponding one of the annular channels 132.

In use to carry out the methodology of the present invention, fluid to be treated is pumped into the inlet port 129 and moves along the reactor 119 to be extracted at the outlet port 131. As best illustrated in FIG. 15, the fluid moves generally in a primary flow 136 along the length of the UV lamp and through the spaces 134, which confine the flow to a region close to the UV source. However, when the primary flow encounters a baffle 133, it is diverted toward the outside of the reaction chamber to a location farther from the UV source. On the other side of the baffle 133, the primary flow is again diverted back toward the UV source, and then flows through the next space 134 to the next succeeding channel and baffle combination.

Thus, it will be seen that the primary flow 136 itself moves repeatedly toward and away from the UV source to obtain benefits of the present invention. In addition, the movement and displacement of the primary flow 136 within each chamber creates circulating secondary flows 137 that are oriented generally transversely relative the UV lamp and thus carry the fluid toward and away from the UV source according to principles of the invention. The circulating secondary flows therefore enhance the cross mixing that characterizes the present invention and results in the benefits thereof.

FIGS. 16 and 17 illustrate still another embodiment of a UV reactor within which the methodology of the present invention may be carried out. The reactor 140 is similar in many respects to the reactor 119 of FIGS. 14 and 15 and includes an elongated UV lamp 141 disposed within a quartz tube 142. A housing 143 surrounds the quartz tube 142 and in conjunction therewith defines a reaction chamber 148. The housing is capped at its top end by a head cap 144 and at its bottom end by a base cap 146, each of which is sealed to the housing and the quartz tube by appropriate O-rings 147. A fluid inlet port 153 communicates with the bottom of the reaction chamber 148 and an outlet port 154 communicates with the top of the reaction chamber for ingress and egress respectively of fluid to be treated.

The inner wall of the housing 143 is machined or otherwise formed with an array of generally annular chambers 149 separated by respective partitions 151. The partitions extend toward but do not engage the quartz tube 142 to define relatively narrow passages 152 between the partitions and the quartz tube. In use, fluid to be treated is pumped through the inlet port 153 and moves upwardly along the length of the UV lamp to be extracted through the outlet port 154. As illustrated in FIG. 17, the fluid moves in a primary flow 156 through the passageways 152 and along the length of the UV lamp 142. The motion of the fluid in the primary flow past successive ones of the annular channels 149 creates vortices that result in circulating secondary flows 157 superimposed on the primary flow within each of the annular chambers. The circulating secondary flows are oriented substantially transversely relative to the UV lamp so that the fluid moves with the secondary flows repeatedly toward and away from the UV lamp according to the methodology of the present invention. The result, again, is even and constant irradiation of the entire volume of fluid with all the attendant benefits thereof as discussed in detail above.

The invention will now be described and further characterized within the context of various examples that represent experiments and clinical trials conducted by the inventors. It will be appreciated that the techniques of and the data presented in conjunction with the examples are not intended to be limiting, but are presented for a better understanding and more complete and enabling disclosure of the methodology of the invention. Many modifications might well be made to the examples presented herein and other experiments not discussed below might be carried out, all within the scope of the present invention.

EXAMPLE 1

Critical Parameters in a Process to Inactivate Virus Particles by UV Radiation.

The goal of viral inactivation by UVC irradiation is to inactivate high levels of virus without damaging the protein or functionality of interest. Two parameters were found to be critical to achieving this goal; namely protein concentration in the fluid, and UV fluency. Fluency is dependent on the physical configuration of the UV irradiator, since internal flow patterns significantly affect the amount of UV light that is received by any given protein molecule or virus panicle in suspension.

Since proteins absorb in the UV range, high protein concentrations can serve to protect the bulk of the target protein from UVC damage. The high protein concentration, however, will also protect the virus. It is necessary therefore to independently evaluate both protein integrity and viral inactivation at varying protein concentrations, and then to select a concentration of protein for the inactivation process that will maximize protection of the integrity of the target protein as well as viral reduction.

Thus, the UVC induced potency loss was determined as a function of protein concentration, as shown in FIG. 18, chart A. The UVC-induced potency loss was least at concentrations of 12.5 mg/ml $\alpha_1$ proteinase inhibitor, but increased at protein concentrations of 7.0, 5.0 and 4.0 mg/ml. The greatest effect on potency was seen at the lowest protein concentration, 2.5 mg/ml. In contrast, as shown in FIG. 9B, the smallest reduction in virus infectivity was observed at the highest $\alpha_1$ proteinase inhibitor concentration of 12.5 mg/ml, and the highest level of inactivation was observed at the lowest concentration, namely 2.5 mg/ml. Based on these data, 5 mg/ml of $\alpha_1$ proteinase inhibitor was used for UVC inactivation as a compromise between acceptable protein potency and good viral inactivation.

Model Virus Studies

Virus Stocks. Porcine Parvovirus (PPV), strain Tennessee, a non-enveloped, single-stranded DNA virus was used in these studies as a model for human parvovirus B19. This virus has been shown to be resistant to inactivation by several methods, including pasteurization and dry heat.

Virus stocks were prepared by infection of porcine testicle (PT) cells. Virus was propagated by infecting subconfluent monolayers of PT cells at a low multiplicity of infection, adding propagation medium and then incubating the cells at 37° C. in 5% $CO_2$ until advanced cytopathology was observed. Virus propagation media consisted of minimum essential medium, Earle's salts supplemented with 7.5% fetal bovine serum and NHG. NHG was added to prevent contamination and provide for the additional media requirements of this cell line and consisted of 0.1 mM nonessential amino acids, 10 mM HEPES (N-[2-Hydroxyethyl]piperazine-N'-[2-ethanesulfonic acid], 0.05 mg/ml gentamicin and fungizone (2.5 mg/ml Amphotericin B). Infected cells were disrupted by freeze-thawing and the cell lysates were stored at about −70° C. until used. The virus spike for each experiment was prepared by thawing the virus-infected cell lysate, centrifuging at low speed (4000×g) to remove the cell debris and collecting the clarified supernatants.

Virus Assay.

Viral inactivation by UVC was determined by endpoint dilution in 96-well microtiter plates seeded with PT cells and using MEM containing 7.5% FBS and NHG. Virus was diluted using serial half log dilutions of the test sample or positive control in Hank's Balanced Salt Solution (HBSS). Positive controls consisted of the same lot of virus that was used as the virus spike. Unspiked HBSS was used as a negative control. Each dilution was used to inoculate 8 wells of a 96-well microtiter plate. After 7 days incubation at 37° C. in 5% $CO_2$, cytopathology was scored. Results were converted into a titer (log median tissue culture infective dose per ml; $TCID_{50}$/ml) by the method of Spearman and Karber (Cavalli-Sfprza, L. *Biometrie Grundzuge biologisch-medizinischer Statistik*[Biometry, the basics of biological and medical statistics], Gustav Fischer Verlag Stuttgart, 1974, p. 171-173.)

A variety of viral species were tested for their relative inactivation susceptibilities.

TABLE 1

Inactivation of virus with varying genome sizes and types of nucleic acid. $D_4$ is defined as the UV dose required to reduce or inactivate the virus by 4 log magnitudes.

| virus | genome size | genome type | envelope | $D_4$ (Joules/cm$^2$) |
| --- | --- | --- | --- | --- |
| PPV | 5 kb | DNA | no | 0.19 |
| SV-40 | 5 kbp | DNA | no | 0.14 |
| polio | 7.7 kb | RNA | no | 1.125 |
| HAV | 7.5 kb | RNA | no | 2.25 |
| FIV | 10 kb | RNA | yes | |
| Sindbis | 11.3 kb | RNA | yes | 1.125 |
| BVDV | 12 kb | RNA | yes | 2.25 |
| Reo | 23.5 kbp | RNA | no | 2.25 |
| Adeno | 36 kbp | DNA | no | 9 |
| PRV | 150 kbp | RNA | yes | 9 |

As shown in Table 1, the processes of the present invention inactivate PPV at a smaller fluency than other viruses, but all were inactivated by at least four orders of magnitude when exposed to fluencies within the range 0.014-9.0 Joules/cm$^2$. Also, the smaller the viral genome, typically the smaller the effective fluency value.

EXAMPLE 2

Protein Integrity.

Following UVC exposure the retention of immunoglobulin integrity was assessed by evaluating the extent of aggregation and fragmentation of the molecule. This was done by size-exclusion HPLC using a TSK-G3000 (Toso-Haas) column and 0.91 M $Na_2HPO_4$, pH 5.2-0.2 M NaCl buffer. Immunoglobulin integrity was expressed as the area percent monomeric protein.

For $\alpha_1$PI, protein integrity was assessed by determining the ability of the enzyme to inhibit porcine elastase. Protein integrity was expressed as the percent of the activity before UVC exposure.

Inactivation of PPV in IGIV.

Figure 19:
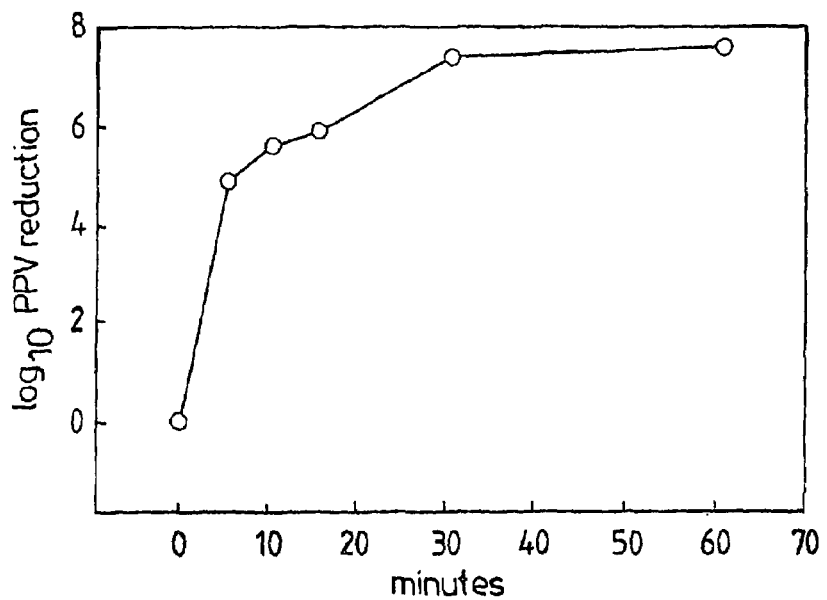
FIG. 19 is a graph showing PPV reduction in a solution of 5 mg/ml of $\alpha_1$PI proteinase inhibitor as a function of time and illustrates the results of a UVC inactivation of IVIG experiment applying the methodology of the present invention.

Pre-formulation IGIV was diluted to 0.8% with water, adjusted to pH 4.2 and spiked to 10% with PPV. To evaluate the effect of UVC exposure on protein integrity, unspiked IGIV solutions were used. Solutions of IGIV were pumped through a tubular UV reactor with a peristaltic pump, calibrated to deliver 100 ml/min. The protein solution was pumped through the device and re-circulated through a stirred reservoir containing the sample. The protein solution was re-circulated though the entire assembly for 5, 10, 15, 30 and 60 minutes, corresponding to fluencies of 2.8, 5.6, 8.4, 16.9 and 33.8 Joules/cm$^2$, respectively. In this case fluency was defined as the mean residence time (reactor volume divided by volume flow rate) multiplied by the UV light intensity at the surface of the reaction chamber nearest the UV source (which may be the surface of a quartz sleeve surrounding the UV lamp). For these calculations, ideal plug flow was assumed. As shown in FIG. 19, after 5 minutes of re-circulation, four logs of PPV reduction was observed, and by 30 minutes, over seven logs of inactivation was seen. After 60 minutes of UVC exposure, 95% monomeric IgG remained.

EXAMPLE 3

Inactivation of PPV in Alpha$_1$ Proteinase Inhibitor.

Alpha$_1$ proteinase inhibitor ($\alpha_1$PI) was diluted to 5 mg/ml in 20 mM Na phosphate, pH 7.0 and 100 mM NaCl and exposed to UVC in the same device as used in example 1. During this experiment, however, the solution was pumped through the device in a single pass at flow rates between 25 and 1200 ml/minutes, resulting in fluencies ranging from 0.19-18 Joules/cm$^2$.

To evaluate virus reduction, the protein solution was spiked to 10% with PPV and to evaluate protein integrity, unspiked solutions were exposed to UVC. As is also shown in Table 2 at higher fluencies PPV was reduced to a level below that of detection; variation in log reduction was observed due to variation in starting titers of the spiking virus. At least 95% of $\alpha_1$PI activity remained after exposure to fluencies less or equal to 2.3 Joules/cm$^2$.

TABLE 2

| Fluency (J/cm$^2$) | Log$_{10}$ PPV Reduction | % Initial $\alpha_1$PI activity |
|---|---|---|
| 18 | 4.2<br>n = 1 | 76.2<br>n = 1 |
| 9 | 4.8 ± 0.9<br>n = 4 | 87.6 ± 2.1<br>n = 4 |
| 4.5 | 5.3 ± 0.4<br>n = 5 | 91.9 ± 4.5<br>n = 7 |
| 2.3 | 5.4 ± 0.1<br>n = 4 | 96.5 ± 1.2<br>n = 2 |
| 1.5 | 5.4 ± 0.1<br>n = 3 | 96.7 ± 3.4<br>n = 3 |
| 1.1 | 5.2 ± 0.1<br>n = 3 | 100<br>n = 1 |
| 1.0 | 4.7 ± 0.4<br>n = 2 | 100.0 ± 0.0<br>n = 2 |
| 0.8 | 4.6 ± 0.4<br>n = 2 | 98.9 ± 1.1<br>n = 2 |
| 0.6 | 3.6<br>n = 1 | ND |
| 0.5 | 2.9 ± 0.4<br>n = 2 | ND |
| 0.38 | 2.6<br>n = 1 | ND |
| 0.3 | 2.6<br>n = 1 | ND |
| 0.49 | 2.1<br>n = 1 | ND |

EXAMPLE 4

Inactivation of PPV in Alpha$_1$ Proteinase Inhibitor.

Figure 20:
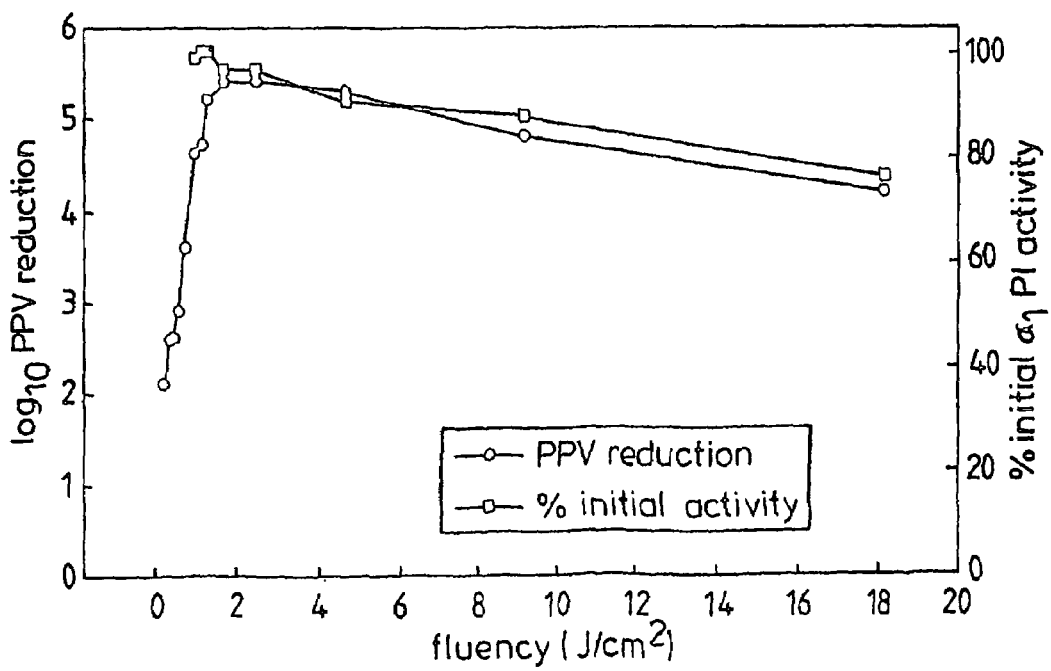
FIG. 20 is a graph of PPV reduction in a solution of 5 mg/ml of $\alpha_1$PI proteinase inhibitor and percent $\alpha_1$PI activity as a function of fluency and illustrates the results of yet another UVC inactivation experiment applying the methodology of the present invention.

Solutions of $\alpha_1$PI that had been diluted to 5 mg/ml in 20 mM Na phosphate, pH 7.0-100 mM NaCl were exposed to UVC in a second type of tubular reactor, wherein the inlet and outlet ports are off-set. This produces a flow pattern that is primarily tangential, but which also contains a radial component to the annular flow in the reactor ("tangential flow reactor"). For evaluation of virus reduction, the protein solutions were spiked to 10% with PPV. The data shown in FIG. 20 indicate that in this reactor four logs of PPV inactivation can be inactivated at lower fluencies than in the tubular reactor used in Examples 10 and 11. At least 95% of the initial $\alpha_1$PI activity was observed at fluencies that were less than or equal to 2 Joules/cm$^2$. Since the same UV lamp and the same light intensity was used in all of the experiments, this demonstrates that improved hydrodynamic conditions (mixing), i.e. inducing a circulating secondary flow within the primary flow, reduce the total residence time of protein solution in the reactor that is necessary to gain adequate virus inactivation.

EXAMPLE 5

Figure 22:
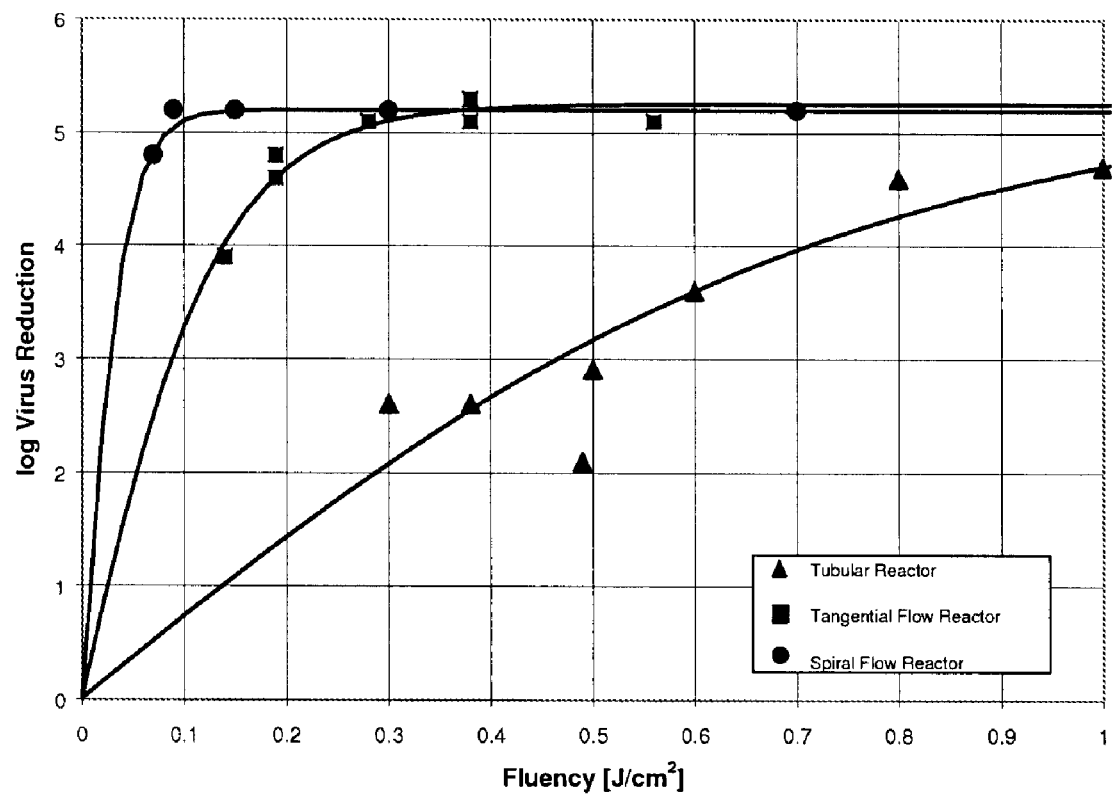
FIG. 22 is a graph of the result of studies evaluating the inactivation of porcine parvo virus (PPV) in a solution of 5 mg/ml alpha$_1$ proteinase inhibitor in three different reactor configurations.

FIG. 22 shows the result of studies evaluating the inactivation of porcine parvo virus (PPV) in a solution of 5 mg/ml alpha$_1$ proteinase inhibitor in three different reactor configurations. It can be seen that a threshold of 4-log virus reduction can be achieved at an approximate fluency of 0.7 J/cm$^2$ in a simple tubular reactor, similar the prior art reactor shown in FIG. 1. Improved hydrodynamic conditions, especially an increase in radial flow components in a reactor with tangential flow characteristics and a reactor with a spiral wound reaction chamber (see FIG. 8) lead to a significant decrease in UV light energy that is necessary to sterilize plasma solutions. These data demonstrate that 4-logs of PPV inactivation can be achieved at approximately 0.15 J/cm$^2$ in a tubular reactor with tangential inlet and outlet a. In a reactor with spiral wound reaction chamber less than 0.1 J/cm$^2$ are sufficient to inactivate 4-log of PPV. It should be noted that log reduction values between 4.5 and 5 may approach the detection limit of the virus assay and the actual virus reduction may even be higher.

Figure 23:
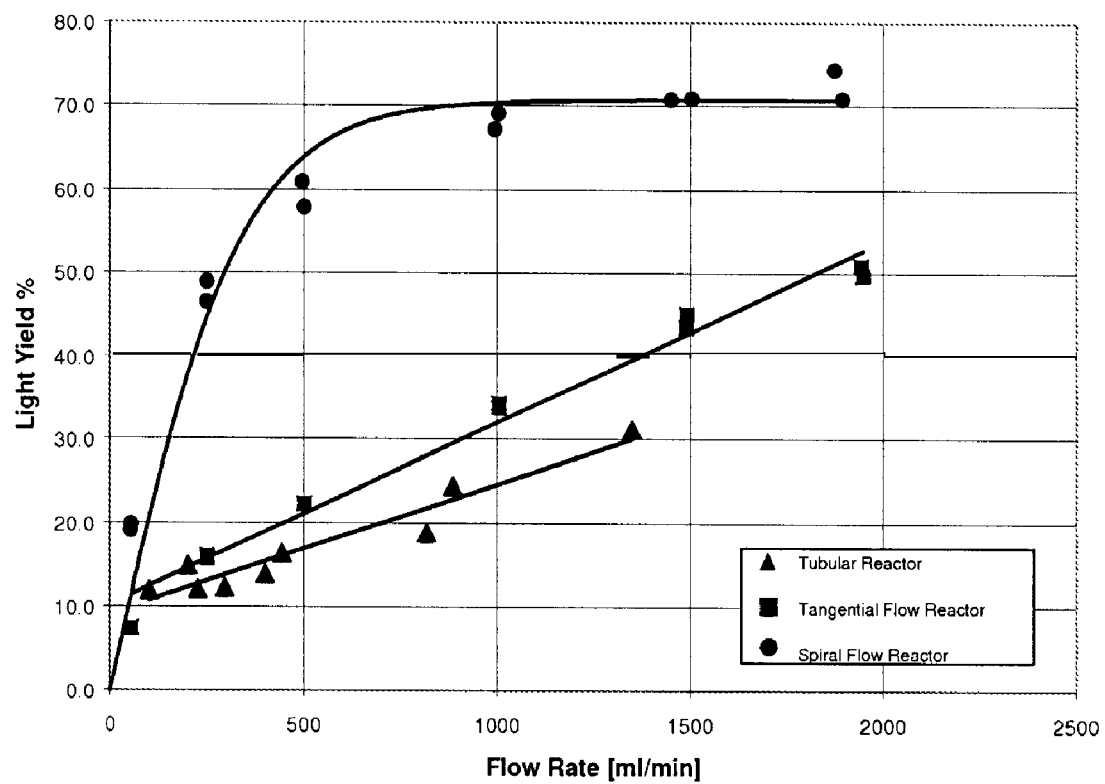
FIG. 23 is a graph of UV light yield as a function of flow rate in three different tubular reactors.

These results are consistent with data generated using a UV photosensitive substance instead of viruses. In this case, the UV induced formation of triiodide ions from iodide ions was used, following an approach described by Rahn (Rahn, R. O.; Photochemistry and Photobiology 58(1993)6, 874-880, ibid 66(1997)4, 450-455). Here, potassium iodide was used as a UV photosensitive component to determine the UV light intensity at 254 nm, delivered to the reaction medium in the same three reactors used in Graph A. Comparison of the measured light intensity with the light intensity that is emitted by the UV bulb gives a UV light yield. Since the penetration depth of UV light into a potassium iodide solution is extremely small (less than 1 mm) under the given conditions, it can be approximated that iodide conversion only occurs directly at the surface of the quartz sleeve that encapsulates the UV bulb. It is obvious therefore that hydrodynamic conditions, especially radial mixing as a result of circulating secondary flow patterns, should determine the light yield. Data shown in FIG. 23 clearly confirm this. Due to superior hydrodynamic conditions the highest light yield can be found in the reactor with a spiral wound reaction chamber, compared to the other two reactors. Data in FIG. 23 show that radial mixing, i.e. an increase in the circulating secondary flow, increases with increasing flow rate. In the reactor with a spiral wound chamber, however, the degree of mixing seems to level off at flow rates higher than 1000 ml/min. Since radial mixing is slightly better in the reactor with tangential inlet and outlet light yield is higher compared to simple tubular reactor.

EXAMPLE 6

Figure 21:
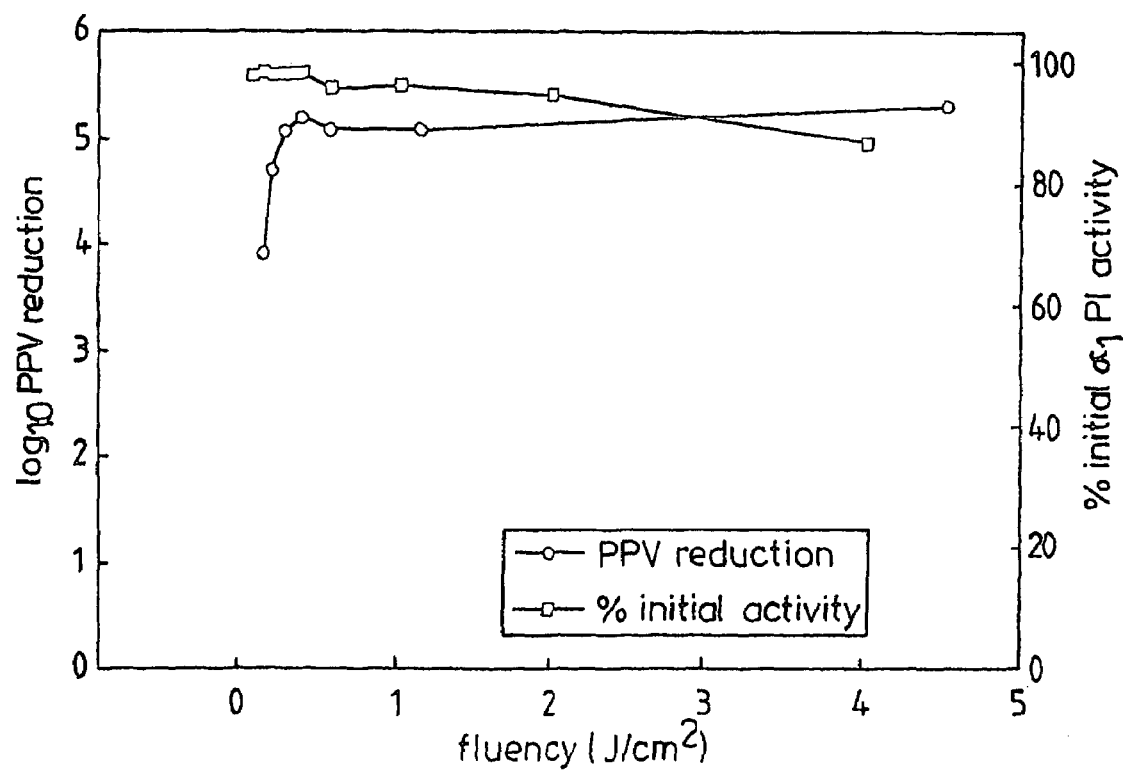
FIG. 21 is a graph of PPV reduction in a solution of 5 mg/ml of $a_1$PI proteinase inhibitor and percent $a_1$PI activity as a function of fluency and illustrates the results of yet another UVC inactivation experiment applying the methodology of the present invention.
Figure 24:
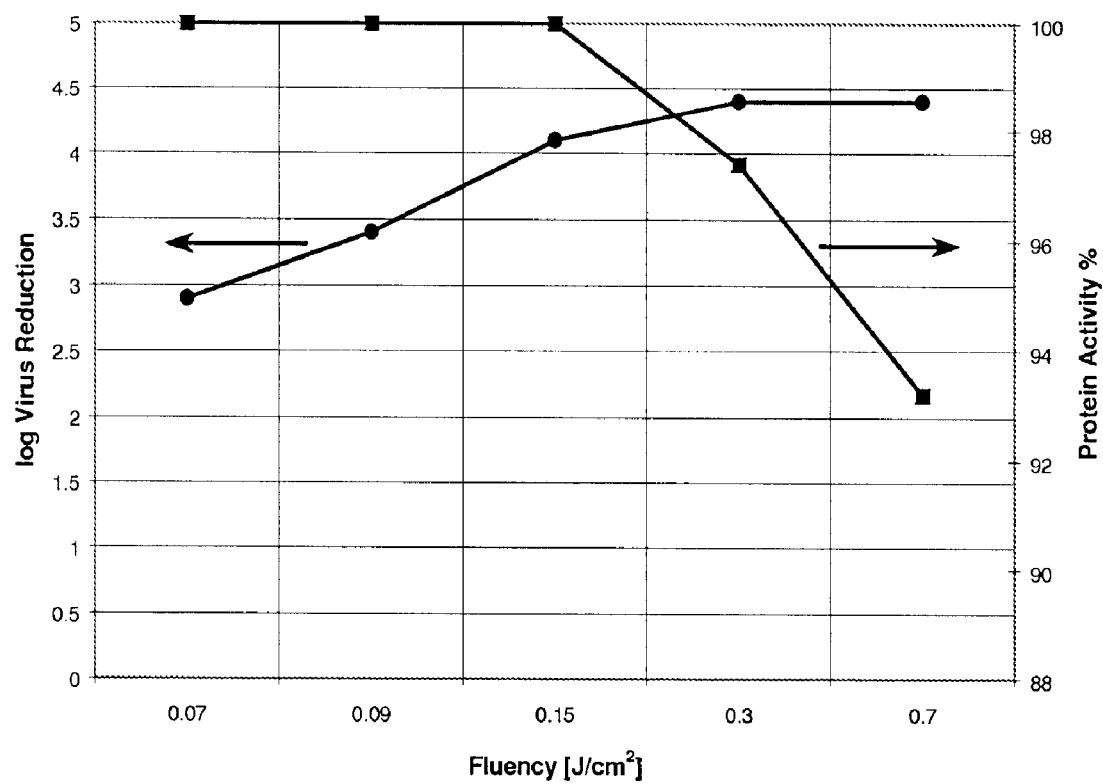
FIG. 24 is a graph of the result of studies assessing the inactivation of Reo-virus 3 in a solution of 5 mg/ml alpha$_1$ proteinase inhibitor in the UV reactor with a spiral wound reaction chamber.

FIG. 24 shows the result of studies assessing the inactivation of Reo-virus 3 in a solution of 5 mg/ml alpha$_1$ proteinase inhibitor in the UV reactor with a spiral wound reaction chamber. It can be seen from this that Reo inactivation increases with increasing fluency and reaches a 4-log reduction at approximately 0.15 J/cm$^2$. At the same time protein activity is not impacted, but it declines at fluencies above 0.15 J/cm$^2$. The fluency value of 0.15 J/cm$^2$ corresponds to a flow rate of 1000 ml/min. As noted in FIG. 21 mixing apparently approaches a limit at flow rates above 1000 ml/min in this device and plateaus. Further increase of flow rate (decreasing of fluency) thus decreases the overall residence time of the virus in the kill zone in the reactor and therefore leads to a reduced virus inactivation. At the same time protein activity declines with reduced flow rates (increasing fluency). This example suggests that there is an optimum flow rate where hydrodynamic conditions are appropriate to assure proper mixing, but at the same time overall residence time is still high enough to effectively kill virus and leave sufficient high protein activity. This flow rate depends not only on reactor design and configuration, as demonstrated, but also on the virus and protein properties and their respective concentrations, as described earlier. Therefore, optimal flow rates need to be determined experimentally for each given system.

The invention has been described herein in terms of preferred embodiments, configurations, methodologies, and examples. It will be understood by those of skill in the art, however, that a variety of additions, deletions, and modifications might well be made to the illustrative embodiments without departing from the spirit and scope of the invention as set forth in the claims.

What is claimed is:

1. A method of irradiating a fluid with ultraviolet radiation from an axially disposed elongated UV source, said method comprising the steps of:
    (a) moving the fluid in a primary axial flow along the UV source; and
    (b) inducing within the moving fluid a circulating secondary flow superimposed on the primary flow, circulating transversally or radially relative to the surface of the UV source, the circulating secondary flow moving the fluid toward and away from the UV source wherein the UV source is at least one elongated UV lamp and wherein step (a) includes defining a reaction chamber surrounding the UV lamp and moving the fluid in a primary flow along the reaction chamber and wherein the circulating secondary flow is achieved by either
        a rotating agitator disposed within the reaction chamber,
        passing the flow through a spiral wound tube surrounding the UV lamp and defining a plurality of individual windings, the windings being formed with a D-shaded cross-section having a rectilinear or flat surface adjacent the UV lamp and a curved outer surface,
        passing the flow through a spiral wound tube surrounding the UV lamp and defining a plurality of individual windings having a rectangular cross section, or
        passing the fluid through a helical channel that spirals continuously around the UV lamp, whereas the helical channel approaches but does not engage the UV lamp and this defines a series of passages between each turn of the helical channel and the UV lamp.

2. The method of claim 1 and wherein the fluid is a biological fluid, the irradiation inactivating microorganisms within the biological fluid.

3. The method of claim 2 and wherein the microorganisms are viruses.

4. The method of claim 1 and wherein the fluid is a foodstuffs fluid.

5. A method for inactivating microorganisms in a fluid contaminated with microorganisms, said method comprising the steps of:
    (a) providing a reactor for radiating ultraviolet light into said fluid, the reactor having a reaction chamber connected to at least one inlet and one outlet for the fluid, and an ultraviolet radiation source;
    (b) moving the fluid through the reaction chamber in a primary flow generally along the ultraviolet radiation source; and
    (c) inducing a circulating secondary flow superimposed on the primary flow, the secondary flow being oriented transversely relative to the ultraviolet radiation source wherein the UV source is at least one elongated UV lamp and wherein step (a) includes defining a reaction chamber surrounding the UV lamp;
    and wherein the circulating secondary flow is induced by either
        a rotating agitator being disposed within the reaction chamber,
        passing the flow through a spiral wound tube surrounding the UV lamp and defining a plurality of individual windings the windings being formed with a generally D-shaded cross section having a generally rectilinear or flat surface adjacent the UV lamp and a curved outer surface,
        passing the flow through a spiral wound tube surrounding the UV lamp and defining a plurality of individual windings, the windings having a generally rectangular cross section, or
        passing the fluid through a helical channel that spirals continuously around the UV lamp, whereas the helical channel approaches but does not engage the UV lamp and this defines a series of relatively narrow passages between each turn of the helical channel and the UV lamp.

6. The method of claim 5, wherein the microorganism to be inactivated is a virus.

7. The method of claim 6, wherein the fluid is exposed to a viral inactivating less than about 30 Joules/cm$^2$.

8. The method of claim 6, wherein the fluid is exposed to a viral inactivating fluency between about 0.01 Joules/cm$^2$ and about 10 Joules/cm$^2$.

9. The method of claim 6, wherein the fluid is exposed to a viral inactivating fluency between about 0.02 Joules/cm$^2$ and about 5 Joules/cm$^2$.

10. The method of claim 5, wherein the ultraviolet radiation is UVC radiation.

11. The method of claim 5, wherein the wavelength of the ultraviolet radiation is about 254 nm.

* * * * *